US006936424B1

(12) United States Patent
Watkins et al.

(10) Patent No.: US 6,936,424 B1
(45) Date of Patent: Aug. 30, 2005

(54) MATERIALS AND METHODS FOR DETECTION AND TREATMENT OF BREAST CANCER

(75) Inventors: Brynmor Watkins, Waltham, MA (US); Robert P. Szaro, Franklin, MA (US)

(73) Assignee: Matritech, Inc., Newton, MA (US)

( * ) Notice: Subject to any disclaimer, the term of this patent is extended or adjusted under 35 U.S.C. 154(b) by 0 days.

(21) Appl. No.: 09/709,947

(22) Filed: Nov. 10, 2000

Related U.S. Application Data

(60) Provisional application No. 60/201,721, filed on May 3, 2000, provisional application No. 60/178,860, filed on Jan. 27, 2000, provisional application No. 60/172,170, filed on Dec. 17, 1999, and provisional application No. 60/165,173, filed on Nov. 12, 1999.

(51) Int. Cl.[7] .................. G01N 33/53; G01N 33/567; G01N 33/574; G01N 33/48; C12Q 1/00
(52) U.S. Cl. ..................... 435/7.1; 435/4; 435/7.2; 435/7.21; 435/7.23; 436/63; 436/64; 436/86; 436/164; 530/300; 530/350; 530/386; 530/387.1; 530/387.3; 530/387.7; 530/387.9; 530/388.1; 530/388.24; 530/388.25; 530/389.1; 530/389.3; 530/391.1; 530/391.3
(58) Field of Search .................... 530/300, 350, 530/385, 386, 387.1, 387.3, 387.7, 387, 9, 388.1, 388.24, 388.25, 389.1, 389.3, 391.1, 391.3; 435/4, 7.1, 7.2, 7.23, 7.21; 436/63, 64, 86, 164

(56) References Cited

U.S. PATENT DOCUMENTS

| | | | |
|---|---|---|---|
| 5,342,764 A | 8/1994 | Johnson et al. | 435/252.3 |
| 5,561,222 A | 10/1996 | Keene et al. | 530/350 |
| 5,719,060 A | 2/1998 | Hutchens et al. | 436/174 |
| 5,792,664 A | 8/1998 | Chait et al. | 436/89 |
| 5,876,937 A | 3/1999 | Sillekens | 435/6 |
| 5,962,242 A | 10/1999 | Klug | 435/7.93 |
| 6,020,135 A | 2/2000 | Levine et al. | 435/6 |
| 6,197,525 B1 | 3/2001 | Yao et al. | 435/4 |
| 6,225,047 B1 | 5/2001 | Hutchens et al. | 210/656 |
| 6,287,521 B1 | 9/2001 | Quay et al. | 422/101 |
| 6,410,692 B2 | 6/2002 | Stevens | 530/388.25 |
| 2002/0081659 A1 * | 6/2002 | Rosen et al. | |

FOREIGN PATENT DOCUMENTS

| | | | |
|---|---|---|---|
| AU | 720626 | 2/1998 | |
| DE | 196 32 521 A | 2/1998 | |
| EP | 0 460 607 A2 | 11/1991 | ........... C12P/21/08 |
| WO | WO 98/42725 | 1/1998 | ........... C07H/21/02 |
| WO | WO 98/07036 | 2/1998 | ........... G01N/33/68 |
| WO | WO 99/39204 | 8/1999 | |
| WO | WO 01/36470 A3 | 5/2001 | |
| WO | WO 01/36470 A2 | 5/2001 | |
| WO | WO 01/36977 A2 | 5/2001 | |
| WO | WO 01/36977 A3 | 5/2001 | |

OTHER PUBLICATIONS

Adams et al. Detection of Mr 24,000 estrogen–regulated protein in human breast cancer by monoclonal antibodies. Cancer Research 43(9): 4297–4301, 1983.*
GenCore databases, Sequence alignment between SEQ ID NO: 1 and sequence 687 of US Paten Application 2002/0081659, Jun. 2002.*
Bringmann et al., (1983) "5'–Terminal Caps of snRNAs Are Accessible for Reaction with 2,2,7–Trimethylguanosine–specific Antibody in Intact snRNPs*," *J. Biol. Chem*, 258(5): 2745–2747.
Brown et al., (2001) "Hypoxia and oxidation stress in breast cancer: Oxidative stress: its effects on the growth, metastatic potential and response to therapy of breast cancer," *Breast Cancer Res.*, 3(5): 323–327.
Casciola–Rosen et al., (1994) "Autoantigens Targeted in Systemic Lupus Erythematosus Are Clustered in Two Populations of Surface structures on Apoptotic Keratinocytes," *J. Exp. Med.*, 179: 1317–1330.
Craft et al., (1988) "The U2 Small Nuclear Ribonucleoprotein Particle as an Autoantigen: Analysis with Sera from Patients with Overlap Syndromes," *J. Clin. Invest.*, 81: 1716–1724.
El–Hefnawy et al., (2004) "Characterization of Amplifiable, Circulating RNA in Plasma and its Potential as a Tool for Cancer Diagnostics," *Clin. Chem.*, 50(3):564–573.
Ochs et al., (1994) "Coiled bodies in the nucleolus of breast cancer cells," *J. Cell Sci.*, 107: 385–399.
Utz, et al., (2000) "Death, autoantigen modificaitons, and tolerance," *Arthritis Res.*, 2:101–114.
Will et al., (2002) "Characterization of novel SF3B and 17S U2 snRNP proteins, including a human Prp5p homologue and SF3b DEAD–box protein," *EMBO J.*, 21: 4978–4988.
Aleynik et al., "Increased circulating products of lipid peroxidation in patients with alcoholic liver disease," *Alcohol Clin. Exp. Res.*, 22(1):192–196 (Feb. 1998).
Chong et al., "Protein profiles and identification of high performance liquid chromatography isolated proteins of cancer cell lines using matrix–assisted laser desorption/ionization time–of–flight mass spectrometry," *Rapid Commun. Mass. Spectrom.*, 12(24):1986–1993 (1998).

(Continued)

Primary Examiner—Alana M. Harris
(74) Attorney, Agent, or Firm—Goodwin Procter LLP

(57) ABSTRACT

The invention provides a wide range of methods and compositions for detecting and treating breast cancer in an individual. Specifically, the invention provides target breast cancer-associated proteins, which permit a rapid detection, preferably before metastases occur, of breast cancer. The target breast cancer-associated protein may be detected, for example, by reacting the sample with a labeled binding moiety, for example, a labeled antibody capable of binding specifically to the protein. The invention also provides kits useful in the detection of breast cancer in an individual. In addition, the invention provides methods utilizing the breast cancer-associated proteins either as targets for treating breast cancer or as indicators for monitoring the efficacy of such a treatment.

19 Claims, 1 Drawing Sheet

OTHER PUBLICATIONS

Clements et al., "Biochemical characterization of patients and prenatal diagnosis of sialic acid storage disease for three families," *J. Inherit. Metab. Dis.*, 11(1):30–44 (1988).

Cross et al., "The trans–spliceosomal U2 snRNP protein 40K of *Trypanosoma brucei*: cloning and analysis of functional domains reveals homology to a mammalian snRNP protein," *The EMBO Journal*, 12(3):1239–1248 (1993).

Davies, H., "ProteinChip™ Case Study: Identification of a Novel Ligand," http://www.ciphergen.com, (Jun. 16, 1999).

"Discovery of Protein Biomarkers and 'Phenomic Fingerprints' Using SELDI ProteinChip™ System," http:www.ciphergen.com, downloaded Jan. 18, 2000.

Fury et al., "Thirteen Anti–Sm Monoclonal Antibodies Immunoprecipitate the Three Cytoplasmic snRNP Core Protein Precursors in Six Distinct Subsets," *Journal of Autoimmunity*, 12:91–100 (1999).

Gottschalk et al., "Identification by mass spectrometry and functional analysis of novel proteins of the yeast [U4/U6–U5] tri–snRNP," *The EMBO Journal*, 18(16):4535–4548 (1999).

Gozani et al., "Evidence that sequence–independent binding of highly conserved U2 snRNP proteins upstream of the branch site is required for assembly of spliceosomal complex A," *Genes& Development*, 10:233–243 (1996).

Habets et al., "Mapping of B Cell Epitopes on Small Nuclear Ribonucleoproteins that React with Human Autoantibodies as well as with Experimentally–Induced Mouse Monoclonal Antibodies," *The Journal of Immunology*, 143(8):2560–2566 (Oct. 15, 1989).

Halliday et al., "Differentiation of human tumors from nonmalignant tissue by natural–abundance $^{13}$C NMR spectroscopy," *Magn. Reson. Med.*, 7(4):384–411 (1988).

Harper et al., "RNA binding specificity of a *Drosophila*snRNP protein that shares sequence homology with mammalian U1–A and U2–B proteins," *Nucleic Acids Research*, 20(14):3645–3650(1992).

Hong et al., "Association of U2 snRNO with the spliceosomal complex E," *Nucleic Acid Research*, 25(2):354–361 (1997).

Jellum et al., "Profiling cells and body fluids—chromatography and two–dimensional electrophoresis as complementary techniques," *J. Chromatrogr.*, 488(1):105–127 (Mar. 17, 1989).

Jellum, E., "Multi–Component Analyses of Human Body Fluids and Tissues in Health and Disease Using Capillary Gas Chromatography –Mass Spectrometry and High–Resolution Two–dimensional Electrophoresis," *Journal of Chromatography*, 239:29–37 (1982).

Jellum et al., "Clinical Applications of Two–Dimensional Electrophoresis," *Clin. Chem.*, 28(4):876–883 (1982).

Kramer et al., "Combined Biochemical and Electron Microscopic Analyses Reveal the Architecture of the Mammalian U2 snRNP," *The Journal of Cell Biology*, 145(7):1355–1368 (Jun. 28, 1999).

Lalioti et al., "The Gene for Human U2 snRNP Auxiliary Factor Small 35–kDa Subunit (U2AF1) Maps to the Progressive Myoclonus Epilepsy (EPM1) Critical Region on Chromosome 21q22.3," *Genomics*, 33:298–300 (1996).

Lamond et al., "Probing the Structure and Function of U2 snRNP with Antisense Oligonucleotides Made of 2'–OMe RNA," *Cell*, 58:383–390 (Jul. 28, 1989).

Leaves et al., "Pyrolysis mass spectrometry in epidemiological and population genetic studies of *Haemophilus influenzae*," *J. Med. Microbiol.*, 46(3):204–207 (1997).

Lim et al., "Altered hydroxylation of estrogen in patients with postmenopausal osteopenia," *J. Clin. Endocrinol. Metab.*, 82(4):1001–1006 (Apr. 1997).

Loo et al., "High sensitivity mass spectrometric methods for obtaining intact molecular weights from gel–separated proteins," *Electrophoresis*, 20:743–748 (1999).

Lollo et al., "Improved two–dimensional gel electrophoresis representation of serum proteins by using ProtoClear™," *Electrophoresis*, 20:854–859 (1999).

Ogorzalek Loo et al., "Sensitivity and mass accuracy for proteins analyzed directly from polyacrylamide gels: Implications for proteome mapping," *Electrophoresis*, 18:382–390 (1997).

Ogorzalek Loo et al., "Mass Spectrometry of Proteins Directly from Polyacrylamide Gels," *Anal. Chem.*, 68:1910–1917 (1996).

Osin et al., "Experimental pathology and breast cancer genetics: new technologies," *Recent Results Cancer Res.*, 152:35–48 (1998).

Ostergaard et al., "Proteome profiling of bladder squamous cell carcinomas: identification of markers that define their degree of differentiation," *Cancer Res.*, 57(18) 4111–4119 (Sep. 15, 1997).

Rohde et al., "Comparison of protein mixtures in aqueous humor by membrane proconcentration—capillary electrophoresis—mass spectrometry", *Electrophoresis*, 19: 2361–2370 (1998).

Schuhmacher et al., "Investigations concerning the potential for using $^1$H NMR relaxometry or high–resolution spectroscopy of plasma as a screening test for malignant lung disease," *Magn. Reson. Med.*, 13(1):103–132 (1990).

Spector et al., "Differences in snRNP Localization Between Transformed and Nontransformed Cells," *Molecular Biology of the Cell*, 3:555–569 (May 1992).

Thiede et al., "Identification of human myocardial proteins separated by two–dimensional electrophoresis with matrix–assisted laser desorption/ionization mass–spectrometry," *Electrophoresis*, 17(3)588–599 (1996).

Weekes et al., "Bovine dilated cardiomyopathy: Proteomic analysis of an animal model of human dilated cardiomyopathy," *Electrophoresis*, 20:898–906 (1999).

Xu et al., "Synthetic Lethality of Yeast slt Mutations with U2 Small Nuclear RNA Mutations Suggests Functional Interactions between U2 and U5 snRNPs That Are Important for Both Steps of Pre–mRNA Splicing," *Molecular and Cellular Biology*, 18(4):2055–2066 (Apr. 1988).

Bazel et al., "Charaterization of Purified Cathepsin D From Malignant Human Breast Tissue", *International J. of Oncology*, 14(2):315–319 (1999).

Giuffrida et al., "Isolation and Characterization of Full and Truncated Forms of Human Breast Carcinoma Protein BA46 From Human Milk Fat Globule Membranes", *J. of Protein Chemistry*, 17(2): 143–148 (1998).

Alfonso, et al., "Two Monoclonal Antibodies Identifying Human Breast Carcinoma Associated Antigens", *Biotecnologia Aplicada*, 11(1):12–19 (1994).

Autiero et al., "A 17–kDa CD4–binding Glycoprotein Present in Human Seminal Plasma and in Breast Tumor Cells", *Eur. J. Immunol.*, 25(5):1461–1464 (1995).

Alfonso et al., "Monoclonal Antibodies ior cama1 and ior cama2 Identifying Human Breast Carcinoma Associated Antigens", *Inmunologia,13(3)*:102–104 (1994).

Damstrup et al., "Estrogen–Regulated Proteins in Human Breast Cancer: Clinical Value in Advanced Breast Cancer and Correlation with Estrogen Receptor", *Recent Advances in Cellular and Molecular Biology, 4*:243–251 (1992).

Moretti–Rojas et al., "A cDNA for the Estradiol–Regulated 24K Protein: Control of mRNA Levels in MCF–7 Cells", *Breast Cancer Research and Treatment, 11*:155–163 (1988).

Bochert et al., "Molecular Forms of Prostate–Specific Antigen in the Serum of Women with Benign and Malignant Breast Diseases", *British J. of Cancer, 76(8)*:1087–1094 (1997).

Chorvath et al., "Monoclonal Antibodies to Two Adhesive Cell Surface Antigens (CD43 and CD59) with Different Distribution on Hematopoietic and Non–Hematopoietic Tumor Cell Lines", *Neoplasma, 39(6)*:325–329 (1992) (Abstract).

Slentz–Kesler, et al., "Identification and Characterization of K12 (SECTM1), a Novel Human Gene that Encodes a Golgi–Associated Protein with Transmembrane and Secreted Isoforms", *Genomics, 47*:327–340 (1998).

Takei et al., "Partial Purification of Immunoreactive Basic Fibroblast Growth Factors From Sera of Patients with Breast Cancer and Investigation of Their Mitogenic Activity Toward BALB/c3T3 Fibroblasts", *J. of Clinical Biochemistry and Nutrition, 17(1)*:19–28 (1994).

Tachibana et al., "NAG–2 a Novel Transmembrane–4 Superfamily (TM4SF) Protein That Complexes with Integrins and Other TM4SF Proteins", *J. of Biological Chemistry,272(46)*:29181–29189 (1997).

Paweletz et al., "A Novel, Proteomic Approach to Monitor Carcinogenic Disease Progression Using Surface Enhance Desorption Ionization Spectroscopy (SELDI) of Laser Capture Microdissection (LCM)–Derived Cells From Cancer Tissue", *Proceedings of the American Association for Cancer Research, 40*:411, (Mar. 1999) (Abstract).

Paweletz et al., "Rapid Protein Display Profiling of Cancer Progression Directly From Human Tissue Using a Protein Biochip", *Drug Development Research, 49(1)*:34–42 (2000).

International Search Report for International Patent Application PCT/US00/31483.

Chong, et al., "Rapid Screening of Protein Profiles of Human Breast Cancer Cell Lines Using Non–porous Reversed–phase High Performance Liquid Chromatography Separation with Matrix–assisted Laser Desorption/Ionization Time–of–flight Mass Spectral Analysis", *Rapid Communications in Mass Spectrometry, 13*:1808–1812 (1999).

Rasmussen, et al., "Towards a Comprehensive Database of Proteins from the Urine of Patients with Bladder Cancer", *The Journal of Urology, 155*:2113–2119 (Jun. 1996).

P.R. Jungblut, et al., "Proteomics in Human Disease: Cancer, Heart and Infectious Diseases", *Electrophoresis, 20*:2100–2110 (1999).

Habets, et al., "Analysis of a cDNA Clone Expressing a Human Autoimmune Antigen: Full–length Sequence of the U2 Small Nuclear RNA–associated B Antigen", *Proc. Natl. Acad. Sci., USA, 84*:2421–2425 (Apr. 1987).

Watkins, et al., "Surface Enhanced Laser Desorption–Ionization (SELDI) Mass Spectroscopy in the Discovery of Serum Markers for Breast Cancer", *Tumor Biology, 21 (Supplement 1)*: 35 (Sep. 2000). Abstract only.

Watkins, et al., "Identification of Serum Nuclear Matrix Protein Markers of Breast Cancer Using Surface Enhanced Laser Desorption–Ionization (SELDI) Mass Spectroscopy", *Breast Cancer Research and Treatment, 64 (No. 1)*: 98 (Nov. 2000). Abstract only.

Chubb, et al., "Preliminary Study Shows Matritech Identified Breast Cancer Proteins in Blood of all Breast Cancer Patients Tested", *Press Release*, 2 pgs. (Jul. 1, 1999).

Wilusz, et al., "A Multicomponent Complex Is Required for the AAUAAA–Dependent Cross–Linking of a 64–Kilodalton Protein to Polyadenylation Substrates", *Molecular and Cellular Biology*, 1244–1248 (Mar. 1990).

Takagaki, et al., "A Multisubunit Factory, CstF, is Required for Polyadenylation of Mammalian Pre–mRNAs", *Genes and Development*, 2112–2120 (Dec. 1990).

Martincic, et al., "Increase in the 64–kDa Subunit of the Polyadenylation/Cleavage Stimulatory Factor During the $G_o$ to S Phase Transition", *Proc. Natl. Acad. Sci. USA, 95*:11095–11100 (Sep. 1998).

Wallace, et al., "Two Distinct Forms of the 64,000 $M_r$ Protein of the Cleavage Stimulation Factor are Expressed in Mouse Male Germ Cells", *Proc. Natl. Acad. Sci. USA, 96*:6763–6768 (Jun. 1999).

Takagaki, et al., "The Human 64–kDa Polyadenylylation Factor Contains a Ribonucleoprotein–Type RNA Binding Domain and Unusual Auxiliary Motifs", *Proc. Natl. Acad. Sci. USA, 89*:1403–1407 (Feb. 1992).

Takagaki, et al., "A Polyadenylation Factor Subunit is the Human Homologue of the Drosophila Suppressor of Forked Protein", *Nature, 372*:471–474 (Dec. 1, 1994).

Barbaux, et al., "The Xenopus laevis Homologue of the 64–kDa Subunit of Cleavage Stimulation Factor", *Comp. Biochem. Physiol., 114B(3 )*: 313–315 (1996).

Takagaki et al., "Complex Protein Interactions Within the Human Polyadenylation Machinery Identify a Novel Component", *Molecular and Cellular Biology, 20(5)*: 1515–1525 (Mar. 2000).

* cited by examiner

SEQUENCE LISTING

<160> NUMBER OF SEQ ID NOS: 23

<210> SEQ ID NO 1
<211> LENGTH: 13
<212> TYPE: PRT
<213> ORGANISM: Artificial Sequence
<220> FEATURE:
<223> OTHER INFORMATION: Description of Artificial Sequence:Tryptic
      peptide

<400> SEQUENCE: 1

Gln Leu Gln Gly Phe Pro Phe Tyr Gly Lys Pro Met Arg
 1               5                  10

<210> SEQ ID NO 2
<211> LENGTH: 18
<212> TYPE: PRT
<213> ORGANISM: Artificial Sequence
<220> FEATURE:
<223> OTHER INFORMATION: Description of Artificial Sequence:Tryptic
      peptide

<400> SEQUENCE: 2

His Asp Ile Ala Phe Val Glu Phe Glu Asn Asp Gly Gln Ala Gly Ala
 1               5                  10                  15

Ala Arg

<210> SEQ ID NO 3
<211> LENGTH: 23
<212> TYPE: PRT
<213> ORGANISM: Artificial Sequence
<220> FEATURE:
<223> OTHER INFORMATION: Description of Artificial Sequence:Tryptic
      peptide

<400> SEQUENCE: 3

Leu Val Pro Gly Arg His Asp Ile Ala Phe Val Glu Phe Glu Asn Asp
 1               5                  10                  15

Gly Gln Ala Gly Ala Ala Arg
                20

<210> SEQ ID NO 4
<211> LENGTH: 11
<212> TYPE: PRT
<213> ORGANISM: Artificial Sequence
<220> FEATURE:
<223> OTHER INFORMATION: Description of Artificial Sequence:Tryptic
      peptide

<400> SEQUENCE: 4

Thr Val Glu Gln Thr Ala Thr Thr Thr Asn Lys
 1               5                  10

<210> SEQ ID NO 5
<211> LENGTH: 225
<212> TYPE: PRT
<213> ORGANISM: Homo sapiens

<400> SEQUENCE: 5

Met Asp Ile Arg Pro Asn His Thr Ile Tyr Ile Asn Asn Met Asn Asp
 1               5                  10                  15

Lys Ile Lys Lys Glu Glu Leu Lys Arg Ser Leu Tyr Ala Leu Phe Ser
                20                  25                  30

```
Gln Phe Gly His Val Asp Ile Val Ala Leu Lys Thr Met Lys Met
         35                  40                  45
Arg Gly Gln Ala Phe Val Ile Phe Lys Glu Leu Gly Ser Ser Thr Asn
     50                  55                  60
Ala Leu Arg Gln Leu Gln Gly Phe Pro Phe Tyr Gly Lys Pro Met Arg
 65                  70                  75                  80
Ile Gln Tyr Ala Lys Thr Asp Ser Asp Ile Ile Ser Lys Met Arg Gly
                 85                  90                  95
Thr Phe Ala Asp Lys Glu Lys Lys Glu Lys Lys Lys Ala Lys Thr
            100                 105                 110
Val Glu Gln Thr Ala Thr Thr Asn Lys Lys Pro Gly Gln Gly Thr
            115                 120                 125
Pro Asn Ser Ala Asn Thr Gln Gly Asn Ser Thr Pro Asn Pro Gln Val
 130                 135                 140
Pro Asp Tyr Pro Pro Asn Tyr Ile Leu Phe Leu Asn Asn Leu Pro Glu
 145                 150                 155                 160
Glu Thr Asn Glu Met Met Leu Ser Met Leu Phe Asn Gln Phe Pro Gly
                 165                 170                 175
Phe Lys Glu Val Arg Leu Val Pro Gly Arg His Asp Ile Ala Phe Val
            180                 185                 190
Glu Phe Glu Asn Asp Gly Gln Ala Gly Ala Ala Arg Asp Ala Leu Gln
            195                 200                 205
Gly Phe Lys Ile Thr Pro Ser His Ala Met Lys Ile Thr Tyr Ala Lys
            210                 215                 220
Lys
225

<210> SEQ ID NO 6
<211> LENGTH: 9
<212> TYPE: PRT
<213> ORGANISM: Artificial Sequence
<220> FEATURE:
<223> OTHER INFORMATION: Description of Artificial Sequence:tryptic
      peptide

<400> SEQUENCE: 6

Gly Gln Val Pro Met Gln Asp Pro Arg
 1               5

<210> SEQ ID NO 7
<211> LENGTH: 11
<212> TYPE: PRT
<213> ORGANISM: Artificial Sequence
<220> FEATURE:
<223> OTHER INFORMATION: Description of Artificial Sequence:tryptic
      peptide

<400> SEQUENCE: 7

Gly Ser Leu Pro Ala Asn Val Pro Thr Pro Arg
 1               5                  10

<210> SEQ ID NO 8
<211> LENGTH: 11
<212> TYPE: PRT
<213> ORGANISM: Artificial Sequence
<220> FEATURE:
<223> OTHER INFORMATION: Description of Artificial Sequence:tryptic
      peptide

<400> SEQUENCE: 8

Gly Leu Leu Gly Asp Ala Pro Asn Asp Pro Arg
```

-continued

<210> SEQ ID NO 9
<211> LENGTH: 12
<212> TYPE: PRT
<213> ORGANISM: Artificial Sequence
<220> FEATURE:
<223> OTHER INFORMATION: Description of Artificial Sequence:tryptic
      peptide

<400> SEQUENCE: 9

Ala Gly Leu Thr Val Arg Asp Pro Ala Val Asp Arg
 1               5                  10

<210> SEQ ID NO 10
<211> LENGTH: 13
<212> TYPE: PRT
<213> ORGANISM: Artificial Sequence
<220> FEATURE:
<223> OTHER INFORMATION: Description of Artificial Sequence:tryptic
      peptide

<400> SEQUENCE: 10

Ala Leu Arg Val Asp Asn Ala Ala Ser Glu Lys Asn Lys
 1               5                  10

<210> SEQ ID NO 11
<211> LENGTH: 14
<212> TYPE: PRT
<213> ORGANISM: Artificial Sequence
<220> FEATURE:
<223> OTHER INFORMATION: Description of Artificial Sequence:tryptic
      peptide

<400> SEQUENCE: 11

Gly Gly Thr Leu Leu Ser Val Thr Gly Glu Val Glu Pro Arg
 1               5                  10

<210> SEQ ID NO 12
<211> LENGTH: 13
<212> TYPE: PRT
<213> ORGANISM: Artificial Sequence
<220> FEATURE:
<223> OTHER INFORMATION: Description of Artificial Sequence:tryptic
      peptide

<400> SEQUENCE: 12

Asp Ile Phe Ser Glu Val Gly Pro Val Val Ser Phe Arg
 1               5                  10

<210> SEQ ID NO 13
<211> LENGTH: 15
<212> TYPE: PRT
<213> ORGANISM: Artificial Sequence
<220> FEATURE:
<223> OTHER INFORMATION: Description of Artificial Sequence:tryptic
      peptide

<400> SEQUENCE: 13

Gly Ile Asp Ala Arg Gly Met Glu Ala Arg Ala Met Glu Ala Arg
 1               5                  10                  15

<210> SEQ ID NO 14
<211> LENGTH: 15
<212> TYPE: PRT
<213> ORGANISM: Artificial Sequence
<220> FEATURE:
<223> OTHER INFORMATION: Description of Artificial Sequence:tryptic

```
                                peptide

<400> SEQUENCE: 14

Gly Met Glu Ala Arg Ala Met Glu Ala Arg Gly Leu Asp Ala Arg
 1               5                  10                  15

<210> SEQ ID NO 15
<211> LENGTH: 15
<212> TYPE: PRT
<213> ORGANISM: Artificial Sequence
<220> FEATURE:
<223> OTHER INFORMATION: Description of Artificial Sequence:tryptic
      peptide

<400> SEQUENCE: 15

Ala Val Ala Ser Leu Pro Pro Glu Gln Met Phe Glu Leu Met Lys
 1               5                  10                  15

<210> SEQ ID NO 16
<211> LENGTH: 15
<212> TYPE: PRT
<213> ORGANISM: Artificial Sequence
<220> FEATURE:
<223> OTHER INFORMATION: Description of Artificial Sequence:tryptic
      peptide

<400> SEQUENCE: 16

Ala Met Glu Ala Arg Ala Met Glu Val Arg Gly Met Glu Ala Arg
 1               5                  10                  15

<210> SEQ ID NO 17
<211> LENGTH: 21
<212> TYPE: PRT
<213> ORGANISM: Artificial Sequence
<220> FEATURE:
<223> OTHER INFORMATION: Description of Artificial Sequence:tryptic
      peptide

<400> SEQUENCE: 17

Gly Tyr Leu Gly Pro Pro His Gln Gly Pro Pro Met His His Val Pro
 1               5                  10                  15

Gly His Glu Ser Arg
            20

<210> SEQ ID NO 18
<211> LENGTH: 24
<212> TYPE: PRT
<213> ORGANISM: Artificial Sequence
<220> FEATURE:
<223> OTHER INFORMATION: Description of Artificial Sequence:tryptic
      peptide

<400> SEQUENCE: 18

Gly Pro Ile Pro Ser Gly Met Gln Gly Pro Ser Pro Ile Asn Met Gly
 1               5                  10                  15

Ala Val Val Pro Gln Gly Ser Arg
            20

<210> SEQ ID NO 19
<211> LENGTH: 21
<212> TYPE: PRT
<213> ORGANISM: Artificial Sequence
<220> FEATURE:
<223> OTHER INFORMATION: Description of Artificial Sequence:tryptic
      peptide

<400> SEQUENCE: 19
```

```
Asn Met Leu Leu Gln Asn Pro Gln Leu Ala Tyr Ala Leu Leu Gln Ala
  1               5                  10                  15

Gln Val Val Met Arg
            20

<210> SEQ ID NO 20
<211> LENGTH: 22
<212> TYPE: PRT
<213> ORGANISM: Artificial Sequence
<220> FEATURE:
<223> OTHER INFORMATION: Description of Artificial Sequence:tryptic
      peptide

<400> SEQUENCE: 20

Gly Gly Pro Leu Pro Glu Pro Arg Pro Leu Met Ala Glu Pro Arg Gly
  1               5                  10                  15

Pro Met Leu Asp Gln Arg
            20

<210> SEQ ID NO 21
<211> LENGTH: 28
<212> TYPE: PRT
<213> ORGANISM: Artificial Sequence
<220> FEATURE:
<223> OTHER INFORMATION: Description of Artificial Sequence:tryptic
      peptide

<400> SEQUENCE: 21

Ser Leu Gly Thr Gly Ala Pro Val Ile Glu Ser Pro Tyr Gly Glu Thr
  1               5                  10                  15

Ile Ser Pro Glu Asp Ala Pro Glu Ser Ile Ser Lys
            20                  25

<210> SEQ ID NO 22
<211> LENGTH: 500
<212> TYPE: PRT
<213> ORGANISM: Homo sapiens

<400> SEQUENCE: 22

Met Ala Gly Leu Thr Val Arg Asp Pro Ala Val Asp Arg Ser Leu Arg
  1               5                  10                  15

Ser Val Phe Val Gly Asn Ile Pro Tyr Glu Ala Thr Glu Glu Gln Leu
                 20                  25                  30

Lys Asp Ile Phe Ser Glu Val Gly Pro Val Val Ser Phe Arg Leu Val
             35                  40                  45

Tyr Asp Arg Glu Thr Gly Lys Pro Lys Gly Tyr Gly Phe Cys Glu Tyr
         50                  55                  60

Gln Asp Gln Glu Thr Ala Leu Ser Ala Met Arg Asn Leu Asn Gly Arg
 65                  70                  75                  80

Glu Phe Ser Gly Arg Ala Leu Arg Val Asp Asn Ala Ala Ser Glu Lys
                 85                  90                  95

Asn Lys Glu Glu Leu Lys Ser Leu Gly Thr Gly Ala Pro Val Ile Glu
                100                 105                 110

Ser Pro Tyr Gly Glu Thr Ile Ser Pro Glu Asp Ala Pro Glu Ser Ile
            115                 120                 125

Ser Lys Ala Val Ala Ser Leu Pro Pro Glu Gln Met Phe Glu Leu Met
        130                 135                 140

Lys Gln Met Lys Leu Cys Val Gln Asn Ser Pro Gln Glu Ala Arg Asn
145                 150                 155                 160
```

```
Met Leu Leu Gln Asn Pro Gln Leu Ala Tyr Ala Leu Leu Gln Ala Gln
            165                 170                 175

Val Val Met Arg Ile Val Asp Pro Glu Ile Ala Leu Lys Ile Leu His
            180                 185                 190

Arg Gln Thr Asn Ile Pro Thr Leu Ile Ala Gly Asn Pro Gln Pro Val
            195                 200                 205

His Gly Ala Gly Pro Gly Ser Gly Ser Asn Val Ser Met Asn Gln Gln
        210                 215                 220

Asn Pro Gln Ala Pro Gln Ala Gln Ser Leu Gly Gly Met His Val Asn
225                 230                 235                 240

Gly Ala Pro Pro Leu Met Gln Ala Ser Met Gln Gly Gly Val Pro Ala
                245                 250                 255

Pro Gly Gln Met Pro Ala Ala Val Thr Gly Pro Gly Pro Gly Ser Leu
                260                 265                 270

Ala Pro Gly Gly Gly Met Gln Ala Gln Val Gly Met Pro Gly Ser Gly
            275                 280                 285

Pro Val Ser Met Glu Arg Gly Gln Val Pro Met Gln Asp Pro Arg Ala
290                 295                 300

Ala Met Gln Arg Gly Ser Leu Pro Ala Asn Val Pro Thr Pro Arg Gly
305                 310                 315                 320

Leu Leu Gly Asp Ala Pro Asn Asp Pro Arg Gly Gly Thr Leu Leu Ser
                325                 330                 335

Val Thr Gly Glu Val Glu Pro Arg Gly Tyr Leu Gly Pro His Gln
                340                 345                 350

Gly Pro Pro Met His His Val Pro Gly His Glu Ser Arg Gly Pro Pro
                355                 360                 365

Pro His Glu Leu Arg Gly Gly Pro Leu Pro Glu Pro Arg Pro Leu Met
            370                 375                 380

Ala Glu Pro Arg Gly Pro Met Leu Asp Gln Arg Gly Pro Pro Leu Asp
385                 390                 395                 400

Gly Arg Gly Gly Arg Asp Pro Arg Gly Ile Asp Ala Arg Gly Met Glu
                405                 410                 415

Ala Arg Ala Met Glu Ala Arg Gly Leu Asp Ala Arg Gly Leu Glu Ala
            420                 425                 430

Arg Ala Met Glu Ala Arg Ala Met Glu Ala Arg Ala Met Glu Ala Arg
            435                 440                 445

Ala Met Glu Ala Arg Ala Met Glu Val Arg Gly Met Glu Ala Arg Gly
            450                 455                 460

Met Asp Thr Arg Gly Pro Val Pro Gly Pro Arg Gly Pro Ile Pro Ser
465                 470                 475                 480

Gly Met Gln Gly Pro Ser Pro Ile Asn Met Gly Ala Val Val Pro Gln
            485                 490                 495

Gly Ser Arg Gln
            500

<210> SEQ ID NO 23
<211> LENGTH: 577
<212> TYPE: PRT
<213> ORGANISM: Homo sapiens

<400> SEQUENCE: 23

Met Ala Gly Leu Thr Val Arg Asp Pro Ala Val Asp Arg Ser Leu Arg
 1               5                  10                  15

Ser Val Phe Val Gly Asn Ile Pro Tyr Glu Ala Thr Glu Glu Gln Leu
            20                  25                  30
```

-continued

```
Lys Asp Ile Phe Ser Glu Val Gly Pro Val Ser Phe Arg Leu Val
        35                  40                  45
Tyr Asp Arg Glu Thr Gly Lys Pro Lys Gly Tyr Gly Phe Cys Glu Tyr
 50                  55                  60
Gln Asp Gln Glu Thr Ala Leu Ser Ala Met Arg Asn Leu Asn Gly Arg
 65                  70                  75                  80
Glu Phe Ser Gly Arg Ala Leu Arg Val Asp Asn Ala Ala Ser Glu Lys
                 85                  90                  95
Asn Lys Glu Glu Leu Lys Ser Leu Gly Thr Gly Ala Pro Val Ile Glu
            100                 105                 110
Ser Pro Tyr Gly Glu Thr Ile Ser Pro Glu Asp Ala Pro Glu Ser Ile
            115                 120                 125
Ser Lys Ala Val Ala Ser Leu Pro Pro Glu Gln Met Phe Glu Leu Met
            130                 135                 140
Lys Gln Met Lys Leu Cys Val Gln Asn Ser Pro Gln Glu Ala Arg Asn
145                 150                 155                 160
Met Leu Leu Gln Asn Pro Gln Leu Ala Tyr Ala Leu Leu Gln Ala Gln
                165                 170                 175
Val Val Met Arg Ile Val Asp Pro Glu Ile Ala Leu Lys Ile Leu His
                180                 185                 190
Arg Gln Thr Asn Ile Pro Thr Leu Ile Ala Gly Asn Pro Gln Pro Val
            195                 200                 205
His Gly Ala Gly Pro Gly Ser Gly Ser Asn Val Ser Met Asn Gln Gln
            210                 215                 220
Asn Pro Gln Ala Pro Gln Ala Gln Ser Leu Gly Gly Met His Val Asn
225                 230                 235                 240
Gly Ala Pro Pro Leu Met Gln Ala Ser Met Gln Gly Gly Val Pro Ala
                245                 250                 255
Pro Gly Gln Met Pro Ala Ala Val Thr Gly Pro Gly Pro Gly Ser Leu
            260                 265                 270
Ala Pro Gly Gly Gly Met Gln Ala Gln Val Gly Met Pro Gly Ser Gly
            275                 280                 285
Pro Val Ser Met Glu Arg Gly Gln Val Pro Met Gln Asp Pro Arg Ala
            290                 295                 300
Ala Met Gln Arg Gly Ser Leu Pro Ala Asn Val Pro Thr Pro Arg Gly
305                 310                 315                 320
Leu Leu Gly Asp Ala Pro Asn Asp Pro Arg Gly Gly Thr Leu Leu Ser
                325                 330                 335
Val Thr Gly Glu Val Glu Pro Arg Gly Tyr Leu Gly Pro Pro His Gln
            340                 345                 350
Gly Pro Pro Met His His Val Pro Gly His Glu Ser Arg Gly Pro Pro
            355                 360                 365
Pro His Glu Leu Arg Gly Gly Pro Leu Pro Glu Pro Arg Pro Leu Met
            370                 375                 380
Ala Glu Pro Arg Gly Pro Met Leu Asp Gln Arg Gly Pro Pro Leu Asp
385                 390                 395                 400
Gly Arg Gly Gly Arg Asp Pro Arg Gly Ile Asp Ala Arg Gly Met Glu
                405                 410                 415
Ala Arg Ala Met Glu Ala Arg Gly Leu Asp Ala Arg Gly Leu Glu Ala
                420                 425                 430
Arg Ala Met Glu Ala Arg Ala Met Glu Ala Arg Ala Met Glu Ala Arg
            435                 440                 445
```

-continued

```
Ala Met Glu Ala Arg Ala Met Glu Val Arg Gly Met Glu Ala Arg Gly
    450                 455                 460
Met Asp Thr Arg Gly Pro Val Pro Gly Pro Arg Gly Pro Ile Pro Ser
465                 470                 475                 480
Gly Met Gln Gly Pro Ser Pro Ile Asn Met Gly Ala Val Val Pro Gln
                485                 490                 495
Gly Ser Arg Gln Val Pro Val Met Gln Gly Thr Gly Met Gln Gly Ala
            500                 505                 510
Ser Ile Gln Gly Gly Ser Gln Pro Gly Gly Phe Ser Pro Gly Gln Asn
            515                 520             525
Gln Val Thr Pro Gln Asp His Glu Lys Ala Ala Leu Ile Met Gln Val
    530                 535                 540
Leu Gln Leu Thr Ala Asp Gln Ile Ala Met Leu Pro Pro Glu Gln Arg
545                 550                 555                 560
Gln Ser Ile Leu Ile Leu Lys Glu Gln Ile Gln Lys Ser Thr Gly Ala
                565                 570                 575
Pro
```

MATERIALS AND METHODS FOR DETECTION AND TREATMENT OF BREAST CANCER

REFERENCE TO RELATED APPLICATIONS

This application claims the benefit of U.S. Ser. No. 60/165,173, filed Nov. 12, 1999; U.S. Ser. No. 60/172,170, filed Dec. 17, 1999; U.S. Ser. No. 60/178,860, filed Jan. 27, 2000; and U.S. Ser. No. 60/201,721, filed May 3, 2000, the disclosures of which are incorporated by reference herein.

FIELD OF THE INVENTION

The present invention relates generally to methods and compositions for the detection and/or treatment of breast cancer. More specifically, the present invention relates to breast cancer-associated proteins and nucleic acids encoding such proteins which represent cellular markers for breast cancer detection, and molecular targets for breast cancer therapy.

BACKGROUND OF THE INVENTION

Breast cancer is a leading cause of death in women. While the pathogenesis of breast cancer is unclear, transformation of normal breast epithelium to a malignant phenotype may be the result of genetic factors, especially in women under 30 (Miki et al. (1994) *Science* 266: 66–71). However, it is likely that other, non-genetic factors also have a significant effect on the etiology of the disease. Regardless of its origin, breast cancer morbidity increases significantly if it is not detected early in its progression. Thus, considerable effort has focused on the elucidation of early cellular events surrounding transformation in breast tissue. Such effort has led to the identification of several potential breast cancer markers. For example, alleles of the BRCA1 and BRCA2 genes have been linked to hereditary and early-onset breast cancer (Wooster et al. (1994) *Science* 265: 2088–2090). The wild-type BRCA1 allele encodes a tumor suppressor protein. Deletions and/or other alterations in that allele have been linked to transformation of breast epithelium. Accordingly, detection of mutated BRCA1 alleles or their gene products has been proposed as a means for detecting breast, as well as ovarian, cancers (Miki et al., supra). However, BRCA1 is limited as a cancer marker because BRCA1 mutations fail to account for the majority of breast cancers (Ford et al. (1995) *British J. Cancer* 72: 805–812). Similarly, the BRCA2 gene, which has been linked to forms of hereditary breast cancer, accounts for only a small portion of total breast cancer cases (Ford et al., supra).

Several other genes have been linked to breast cancer and may serve as markers for the disease, either directly or via their gene products. Such potential markers include the TP53 gene and its gene product, the p53 tumor suppressor protein (Malkin et al. (1990) *Science* 250: 1233–1238). The loss of heterozygosity in genes such as the ataxia telangiectasia gene has also been linked to a high risk of developing breast cancer (Swift et al. (1991) *N. Engl. J. Med.* 325: 1831–1836). A problem associated with many of the markers proposed to date is that the oncogenic phenotype is often the result of a gene deletion, thus requiring detection of the absence of the wild-type form as a predictor of transformation.

There is, therefore, a need in the art for specific, reliable markers that are differentially expressed in normal and transformed breast tissue and that may be useful in the diagnosis of breast cancer, in the prediction of its onset or the treatment of breast cancer. Such markers and methods for their use are provided herein.

SUMMARY OF THE INVENTION

The invention provides a variety of methods and compositions for detecting the presence of breast cancer in a mammal, for example, a human, and for treating breast cancer in a mammal diagnosed with the disease. The invention is based, in part, upon the discovery of a family of proteins each member of which is detectable at a higher concentration in serum from a mammal, for example, a human, with breast cancer relative to serum from a normal mammal, that is, a mammal without breast cancer. Accordingly, these proteins, as well as nucleic acid sequences encoding such proteins, or sequences complementary thereto, can be used as breast cancer markers useful in diagnosing breast cancer, monitoring the efficacy of a breast cancer therapy and/or as targets of such a therapy.

In one aspect, the invention provides isolated breast cancer-associated protein markers. The protein markers are characterized as being detectable at a higher concentration in the serum of a mammal, specifically, a human, with breast cancer than in serum of a mammal without breast cancer.

One marker protein is further characterized in that it has a molecular weight of about 16 kD, and fails to bind in a detectable amount to an anion exchange resin in the presence of 50 mM sodium phosphate, pH 7.0. This marker protein also has a binding affinity to a nickel SELDI chip.

Another marker protein is further characterized in that it has a molecular weight of about 17 kD, binds to an anion exchange resin in the presence of 50 mM sodium phosphate, pH 7.0, and elutes from the anion exchange resin in the presence of 25 mM sodium chloride in 50 mM sodium phosphate, pH 7.0. This marker protein also has a binding affinity to a WCX-2 SELDI chip.

Another marker protein is further characterized in that it has a molecular weight of about 30 kD, binds to an anion exchange resin in the presence of 50 mM sodium phosphate, pH 7.0, and elutes from the anion exchange resin in the presence of 25 mM sodium chloride in 50 mM sodium phosphate, pH 7.0. This marker protein also has a binding affinity to a WCX-2 SELDI chip.

Another marker protein is further characterized in that it has a molecular weight of about 35 kD, binds to an anion exchange resin in the presence of 50 mM sodium phosphate, pH 7.0, and elutes from the anion exchange resin in the presence of 25 mM sodium chloride in 50 mM sodium phosphate, pH 7.0. This marker protein also has a binding affinity to a WCX-2 SELDI chip.

Another marker protein is further characterized in that it has a molecular weight of about 20 kD, binds to an anion exchange resin in the presence of 50 mM sodium phosphate, pH 7.0, and elutes from the anion exchange resin in the presence of 50 mM sodium chloride in 50 mM sodium phosphate, pH 7.0. This marker protein also has a binding affinity to a nickel SELDI chip.

Another marker protein is further characterized in that it has a molecular weight of about 24 kD, binds to an anion exchange resin in the presence of 50 mM sodium phosphate, pH 7.0, and elutes from the anion exchange resin in the presence of 50 mM sodium chloride in 50 mM sodium phosphate, pH 7.0. This marker protein also has a binding affinity to a nickel SELDI chip.

Another marker protein is further characterized in that it has a molecular weight of about 28 kD, binds to an anion exchange resin in the presence of 50 mM sodium phosphate, pH 7.0, and elutes from the anion exchange resin in the presence of 50 mM sodium chloride in 50 mM sodium phosphate, pH 7.0. This marker protein also has a binding affinity to a nickel SELDI chip. Microsequence analysis has identified the marker protein to be a protein known in the art as small nuclear ribonucleoprotein B" (Habets et al. (1987) PROC NATL ACAD SCI, USA 84, 2421–2425), the amino acid sequence of which is identified hereinbelow as SEQ ID NO: 5.

Another marker protein is farther characterized in that it has a molecular weight of about 35 kD, binds to an anion exchange resin in the presence of 50 mM sodium phosphate, pH 7.0, and elutes from the anion exchange resin in the presence of 50 mM sodium chloride in 50 mM sodium phosphate, pH 7.0. This marker protein also has a binding affinity to a nickel SELDI chip.

Another marker protein is further characterized in that it has a molecular weight of about 35 kD, binds to an anion exchange resin in the presence of 50 mM sodium phosphate, pH 7.0, and elutes from the anion exchange resin in the presence of 50 mM sodium chloride in 50 mM sodium phosphate, pH 7.0. This marker protein also has a binding affinity to a nickel SELDI chip.

Another marker protein is further characterized in that it has a molecular weight of about 18 kD, binds to an anion exchange resin in the presence of 50 mM sodium phosphate, pH 7.0, and elutes from the anion exchange resin in the presence of 100 mM sodium chloride in 50 mM sodium phosphate, pH 7.0. This marker protein also has a binding affinity to a WCX-2 SELDI chip.

Another marker protein is further characterized in that it has a molecular weight of about 71 kD, binds to an anion exchange resin in the presence of 50 mM sodium phosphate, pH 7.0, and elutes from the anion exchange resin in the presence of 100 mM sodium chloride in 50 mM sodium phosphate, pH 7.0. This marker protein also has a binding affinity to a WCX-2 SELDI chip. Microsequence analysis has identified the marker protein to be a protein known in the art as, or related to, the 64 kD subunit of cleavage stimulating factor (Takagaki et al. (1987) PROC NATL ACAD SCI, USA 89, 1403–1407), the amino acid sequence of which is identified hereinbelow as SEQ ID NO: 22 and SEQ ID NO: 23.

Another marker protein is further characterized in that it has a molecular weight of about 12 kD, binds to an anion exchange resin in the presence of 50 mM sodium phosphate, pH 7.0, and elutes from the anion exchange resin in the presence of 150 mM sodium chloride in 50 mM sodium phosphate, pH 7.0. This marker protein also has a binding affinity to a SAX-2 SELDI chip.

Another marker protein is further characterized in that it has a molecular weight of about 42 kD, binds to an anion exchange resin in the presence of 50 mM sodium phosphate, pH 7.0, and elutes from the anion exchange resin in the presence of 200 mM sodium chloride in 50 mM sodium phosphate, pH 7.0. This marker protein also has a binding affinity to a nickel SELDI chip.

Another marker protein is further characterized in that it has a molecular weight of about 56 kD, binds to an anion exchange resin in the presence of 50 mM sodium phosphate, pH 7.0, and elutes from the anion exchange resin in the presence of 200 mM sodium chloride in 50 mM sodium phosphate, pH 7.0. This marker protein also has a binding affinity to a nickel SELDI chip.

Another marker protein is further characterized in that it has a molecular weight of about 35 kD, binds to an anion exchange resin in the presence of 50 mM sodium phosphate, pH 7.0, and elutes from the anion exchange resin in the presence of 400 mM sodium chloride in 50 mM sodium phosphate, pH 7.0. This marker protein also has a binding affinity to a copper SELDI chip.

Furthermore, the aforementioned breast cancer-associated proteins are further characterized as being non-immunoglobulin and/or non-albumin proteins. Furthermore, the breast cancer-associated proteins may further define an antigenic region or epitope that may bind specifically to a binding moiety, for example, an antibody, for example, a monoclonal or a polyclonal antibody, an antibody fragment thereof, or a biosynthetic antibody binding site directed against the antigenic region or epitope. In addition, the invention enables one skilled in the art to isolate nucleic acids encoding the aforementioned breast cancer-associated proteins or nucleic acids capable of hybridizing under specific hybridization conditions to a nucleic acid encoding the breast cancer-associated proteins. Furthermore, the skilled artisan may produce nucleic acid sequences encoding the entire isolated marker protein, or fragments thereof, using methods currently available in the art (see, for example, Sambrook et al., eds. (1989) "Molecular Cloning: A Laboratory Manual," Cold Spring Harbor Press). For example, the breast cancer-associated protein of the invention, when isolated, can be sequenced using conventional peptide sequencing protocols. Based on the peptide sequence, it is possible to produce oligonucleotide hybridization probes useful in screening a cDNA library. The cDNA library may then be screened with the resultant oligonucleotide to isolate full or partial length cDNA sequences encoding the isolated protein.

In another aspect, the invention provides a variety of methods, for example, protein or nucleic acid-based methods, for detecting the presence of breast cancer in a mammal. The methods of the invention may be performed on any relevant tissue or body fluid sample. For example, methods of the invention may be performed on breast tissue, more preferably breast biopsy tissue. Alternatively, the methods of the invention may be performed on a human body fluid sample selected from the group consisting of: blood; serum; plasma; fecal matter; urine; vaginal secretion; spinal fluid; saliva; ascitic fluid; peritoneal fluid; sputum; and breast exudate. It is contemplated, however, that the methods of the invention also may be useful in detecting metastasized breast cancer cells in other tissue or body fluid samples. Detection of breast cancer can be accomplished using any one of a number of assay methods well known and used in the art.

In one aspect, the method of diagnosing cancer in an individual comprises contacting a sample from the individual with a first binding moiety that binds specifically to a breast-cancer associated protein to produce a first binding moiety-cancer-associated protein complex. The first binding moiety is capable of binding specifically to at least one of the breast cancer associated marker proteins identified hereinabove to produce a complex. Thereafter the presence and/or amount of marker protein in the complex can then be detected, for example, via the first binding moiety if labeled with a detectable moiety, for example, a radioactive or fluorescent label, or a second binding moiety labeled with a detectable moiety that binds specifically to the first binding moiety using conventional methodologies well known in the art. The presence or amount of the marker protein can thus be indicative of the presence of breast cancer in the individual. For example, the amount of marker protein in the sample may be compared against a threshold value previously calibrated to indicate the presence or absence of breast cancer, wherein the amount of the complex in the sample relative to the threshold value can be indicative of the presence or absence of cancer in the individual. Although such a method can be performed on tissue, for example, breast tissue, or a body fluid, for example, serum, a body fluid currently is the preferred test sample.

Detection of the aforementioned nucleic acid molecules can also serve as an indicator of the presence of breast cancer and/or metastasized breast cancer in an individual. Accordingly, in another aspect, the invention provides another method for detecting breast cancer in a human. The method comprises the step of detecting the presence of a nucleic acid molecule in a tissue or body fluid sample thereby to indicate the presence of breast cancer in an individual. The nucleic acid molecule is selected from the group consisting of (i) a nucleic acid molecule comprising a sequence capable of recognizing and being specifically bound by a breast cancer-associated protein, and (ii) a nucleic acid molecule comprising a sequence encoding at least a portion of one or more of the breast cancer-associated proteins identified herein.

In one embodiment, the method comprises exposing a sample from the individual under specific hybridization conditions to a nucleic acid probe, for example, greater than about 10 and more preferably greater than 15 nucleotides in length, capable of hybridizing to a target nucleic acid encoding one of the breast cancer-associated proteins identified herein to produce a duplex. Thereafter, the presence of the duplex can be detected using a variety of detection methods known and used in the art. It is contemplated that the target nucleic acid may be amplified, for example, via conventional polymerase chain reaction (PCR) or reverse transcriptase polymerase chain reaction (RT-PCR) methodologies, prior to hybridization with the nucleic acid probe.

In one embodiment, the target nucleic acid (for example, a messenger RNA (mRNA) molecule), is greater than 15 nucleotides, more preferably greater than 50 nucleotides, and most preferably greater than 100 nucleotides in length and encodes an amino acid sequence present in one of the breast cancer-associated proteins identified herein. Such a target mRNA may then be detected, for example, by Northern blot analysis by reacting the sample with a labeled hybridization probe, for example, a $^{32}P$ labeled oligonucleotide probe, capable of hybridizing specifically with at least a portion of the nucleic acid molecule encoding the marker protein. Detection of a nucleic acid molecule either encoding a breast cancer-associated protein or capable of being specifically bound by a breast cancer-associated protein, can thus serve as an indicator of the presence of a breast cancer in the individual being tested.

In another aspect, the invention provides a kit for detecting the presence of breast cancer or for evaluating the efficacy of a therapeutic treatment of a breast cancer. Such kits may comprise, in combination, (i) a receptacle for receiving a human tissue or body fluid sample from the individual to be tested, (ii) a binding partner which binds specifically either to an epitope on a breast cancer-associated marker protein or a nucleic acid sequence encoding at least a portion of the breast cancer-associated protein or the nucleic acid sequence encoding at least a portion of the breast cancer-associated protein, and (iii) a reference sample. In one embodiment, the reference sample may comprise a negative and/or positive control. In that embodiment, the negative control would be indicative of a normal breast cell type and the positive control would be indicative of breast cancer.

In another aspect, the invention provides methods and compositions for treating breast cancer. In one aspect the invention provides proteins or nucleobase-containing sequences useful in the treatment of breast cancer. The therapeutic protein could be, for example, a binding moiety, for example, an antibody, for example, a monoclonal antibody, an antigenic binding fragment thereof, or a biosynthetic antibody binding site capable of binding specifically to a breast cancer-associated protein identified herein. The method comprises the step of administering to a patient with breast cancer, a therapeutically-effective amount of a compound, preferably an antibody, and most preferably a monoclonal antibody, which binds specifically to a target breast cancer-associated protein thereby to inactivate or reduce the biological activity of the protein. The target protein may be any of the breast cancer-associated proteins identified herein. Similarly, it is contemplated that the compound may comprise a small molecule, for example, a small organic molecule, which inhibits or reduces the biological activity of the target breast cancer-associated protein.

In another aspect, the invention provides another method for treating breast cancer. The method comprises the step of administering to a patient diagnosed as having breast cancer, a therapeutically-effective amount of a compound which reduces in vivo the expression of a target breast cancer-associated protein thereby to reduce in vivo the expression of the target protein. In a preferred embodiment, the compound is a nucleobase containing sequence, for example, an anti-sense nucleic acid sequence or a peptidyl nucleic acid (PNA) capable of binding to and reducing the expression (for example, transcription or translation) of a nucleic acid encoding at least a portion of at least one of the breast cancer-associated proteins identified herein. After administration, the anti-sense nucleic acid sequence or the anti-sense PNA molecule binds to the nucleic acid sequences-encoding, at least in part, the target protein thereby to reduce in vivo expression of the target breast cancer-associated protein.

Thus, the invention provides a wide range of methods and compositions for detecting and treating breast cancer in an individual. Specifically, the invention provides breast cancer-associated proteins, which permit specific and early, preferably before metastases occur, detection of breast cancer in an individual. In addition, the invention provides kits useful in the detection of breast cancer in an individual. In addition, the invention provides methods utilizing the breast cancer-associated proteins as targets and indicators, for treating breast cancers and for monitoring of the efficacy of such a treatment. These and other numerous additional aspects and advantages of the invention will become apparent upon consideration of the following figures, detailed description, and claims which follow.

DESCRIPTION OF THE DRAWINGS

The invention can be more completely understood with reference to the following drawings, in which:

FIG. 1A is a spectrum of the heaviest 28 kD protein isolated from the gel, FIG. 1B is a spectrum of the median 28 kD protein isolated from the gel, and FIG. 1C is a spectrum of the lightest 28 kD protein isolated from the gel.

DETAILED DESCRIPTION OF THE INVENTION

Figure 1A:
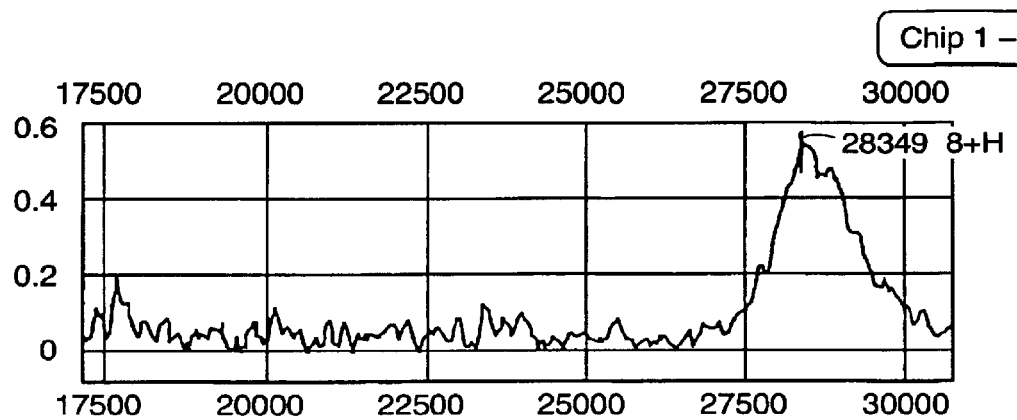
FIGS. 1A–1C are spectra resulting from the characterization via mass spectrometry of 28 kD proteins subjected to trypsin digestion and eluted from a polyacrylamide gel.
Figure 1B:
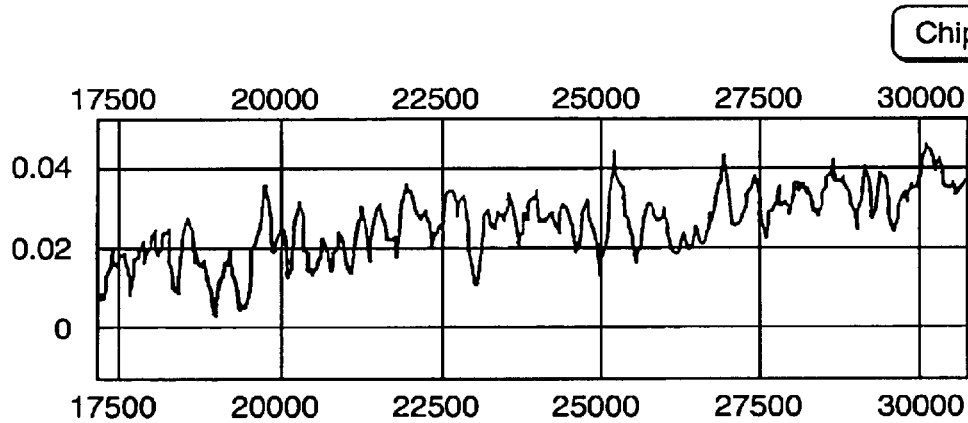
Figure 1C:
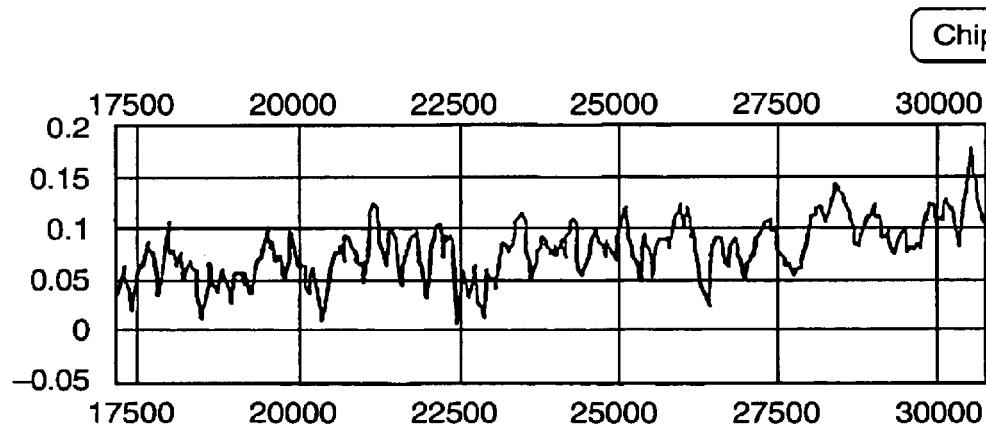

The present invention provides methods and compositions for the detection and treatment of breast cancer. The invention is based, in part, upon the discovery of breast cancer-associated proteins which generally are present at detectably higher levels in serum of humans with breast cancer relative to serum of humans without breast cancer.

The breast cancer-associated proteins or nucleic acids encoding such proteins may act as markers useful in the detection of breast cancer or as targets for therapy of breast cancer. For example, it is contemplated that the marker proteins and binding moieties, for example, antibodies that bind to the marker proteins or nucleic acid probes which hybridize to nucleic acid sequences encoding the marker proteins, may be used to detect the presence of breast cancer in an individual. Furthermore, it is contemplated that the skilled artisan may produce novel therapeutics for treating breast cancer which include, for example: antibodies which can be administered to an individual that bind to and reduce or eliminate the biological activity of the target protein in vivo; nucleic acid or peptidyl nucleic acid sequences which hybridize with genes or gene transcripts encoding the target proteins, thereby to reduce expression of the target proteins in vivo; or small molecules, for example, organic molecules which interact with the target proteins or other cellular moieties, for example, receptors for the target proteins, thereby to reduce or eliminate biological activity of the target proteins.

Set forth below are methods for isolating breast cancer-associated proteins, methods for detecting breast cancer using breast cancer-associated proteins as markers, and methods for treating individuals afflicted with breast cancer using breast cancer-associated proteins as targets for cancer therapy.

1. Methods for Detecting Breast Cancer-Associated Marker Proteins.

Marker proteins of the invention, as disclosed herein, are identified by comparing the protein composition of serum of a human diagnosed with breast cancer with the protein composition of serum of a human free of breast cancer. As used herein, the term "breast cancer-associated protein" is understood to mean any protein which is detectable at a higher level in a tissue or body fluid of an individual diagnosed with breast cancer relative to a corresponding tissue or body fluid of an individual free of breast cancer and includes species and allelic variants thereof and fragments thereof. As used herein, the term "breast cancer" is understood to mean any cancer or cancerous lesion associated with breast tissue or breast tissue cells and can include precursors to breast cancer, for example, atypical ductal hyperplasia or non-atypical hyperplasia. It is not necessary that the marker protein or target molecule be unique to a breast cancer cell or body fluid of an individual afflicted with breast cancer; rather the marker protein or target molecule should have a signal to noise ratio high enough to discriminate between samples originating from a breast cancer tissue or body fluid and samples originating from normal breast tissue or body fluid.

As used herein, a "portion" or a "fragment" of a protein or of an amino acid sequence denotes a contiguous peptide comprising, in sequence, at least ten amino acids from the protein or amino acid sequence (e.g. amino acids 1–10, 34–43, or 127–136 of the protein or sequence). Preferably, the peptide comprises, in sequence, at least twenty amino acids from the protein or amino acid sequence. More preferably, the peptide comprises, in sequence, at least forty amino acids from the protein or amino acid sequence.

The breast cancer-associated marker proteins of the invention were identified by comparing the proteins present in the serum of individuals with breast cancer to the proteins present in the serum of individuals without breast cancer. Albumin and immunoglobulin proteins were removed from the serum, and the proteins were separated into twelve fractions by anion exchange chromatography. Briefly, the proteins were loaded on a strong anion exchange column in the presence of 50 mM sodium phosphate, pH 7.0, and eluted with a stepwise gradient of sodium chloride in 50 mM sodium phosphate, pH 7.0. The resulting twelve fractions include a flow-through fraction, a fraction eluting in 25 mM sodium chloride, a 50 mM fraction, a 75 mM fraction, a 100 mM fraction, a 125 mM fraction, a 150 mM fraction, a 200 mM fraction, a 250 mM fraction, a 300 mM fraction, a 400 mM fraction, and a 2 M fraction.

Each fraction was analyzed by SELDI (surface-enhanced laser desorption and ionization) mass spectrometry. Samples from each of the twelve fractions were applied to one of four different SELDI chip surfaces. A copper or nickel SELDI surface can be generated by adding a copper or nickel salt solution to a chip comprising ethylenediaminetriacetic acid. Other SELDI chip surfaces include: WCX-2 which comprises carboxylate moieties, and SAX-2 which comprises quarternary ammonium moieties. The breast cancer-associated proteins of the invention can therefore be characterized by their increased presence in serum of individuals having breast cancer relative to individuals without breast cancer, their molecular weight, binding and elution characteristics on an anion exchange resin, and their affinity to a particular SELDI chip. For example, as used herein, the term "affinity" to a particular SELDI chip is understood to mean that the breast cancer-associated proteins of the invention bind preferentially to one type of SELDI chip (e.g., copper SELDI chip) relative to one or more of the other SELDI chips (e.g., the nickel, SAX-2 and WCX-2 chips) disclosed herein. As discussed in detail in Example 1, comparison of the sera from diseased and healthy individuals revealed a number of proteins frequently present at detectable levels in the sera of diseased individuals, but infrequently present at comparable levels in the sera of healthy individuals.

Once the breast cancer-associated proteins have been identified by mass spectroscopy, the identified proteins can be isolated by standard protein isolation methodologies and sequenced using protein sequencing technologies known and used in the art. See, for example, Examples 5 and 6. Once the amino acid sequences are identified then nucleic acids encoding the marker proteins or portions thereof can be identified using conventional recombinant DNA methodologies. See, for example, Sambrook et al. eds. (1989) "Molecular Cloning: A Laboratory Manual", Cold Spring Harbor Press. For example, an isolated breast cancer-associated protein can be sequenced using conventional peptide sequencing protocols, and the oligonucleotide hybridization probes designed for sequencing a cDNA library. The cDNA library may then be screened with the resultant hybridization probes to isolate full length or partial length cDNA sequences encoding the isolated marker proteins.

Marker proteins useful in the present invention encompass not only the particular sequences identified herein but also allelic variants thereof and related proteins that also function as marker proteins. Thus, for example, sequences that result from alternative splice forms, post-translational modification, or gene duplication are each encompassed by the present invention. Species variants are also encompassed by this invention where the patient is a non-human mammal. Other homologous proteins that may function as marker proteins are also envisioned. Preferably, variant sequences are at least 80% similar or 70% identical, more preferably at least 90% similar or 80% identical, and most preferably 95% similar or 90% identical to at least a portion of one of the sequences disclosed herein.

To determine whether a candidate peptide region has the requisite percentage similarity or identity to a reference polypeptide or peptide oligomer, the candidate amino acid sequence and the reference amino acid sequence are first aligned using the dynamic programming algorithm described in Smith and Waterman (1981), *J. Mol. Biol.* 147:195–197, in combination with the BLOSUM62 substitution matrix described in FIG. 2 of Henikoff and Henikoff (1992), "Amino acid substitution matrices from protein blocks", *PNAS* (1992 November), 89:10915–10919. For the present invention, an appropriate value for the gap insertion penalty is −12, and an appropriate value for the gap extension penalty is −4. Computer programs performing alignments using the algorithm of Smith-Waterman and the BLOSUM62 matrix, such as the GCG program suite (Oxford Molecular Group, Oxford, England), are commercially available and widely used by those skilled in the art.

Once the alignment between the candidate and reference sequence is made, a percent similarity score may be calculated. The individual amino acids of each sequence are compared sequentially according to their similarity to each other. If the value in the BLOSUM62 matrix corresponding to the two aligned amino acids is zero or a negative number, the pairwise similarity score is zero; otherwise the pairwise similarity score is 1.0. The raw similarity score is the sum of the pairwise similarity scores of the aligned amino acids. The raw score is then normalized by dividing it by the number of amino acids in the smaller of the candidate or reference sequences. The normalized raw score is the percent similarity. Alternatively, to calculate a percent identity, the aligned amino acids of each sequence are again compared sequentially. If the amino acids are non-identical, the pairwise identity score is zero; otherwise the pairwise identity score is 1.0. The raw identity score is the sum of the identical aligned amino acids. The raw score is then normalized by dividing it by the number of amino acids in the smaller of the candidate or reference sequences. The normalized raw score is the percent identity. Insertions and deletions are ignored for the purposes of calculating percent similarity and identity. Accordingly, gap penalties are not used in this calculation, although they are used in the initial alignment.

In all instances, variants of the naturally-occurring sequences, as described above, must be tested for their function as marker proteins. Specifically, their presence or absence in a particular form or in a particular biological compartment must be indicative of the presence or absence of cancer in an individual. This routine experimentation can be carried out by the methods described hereinbelow or by other methods known in the art.

Marker proteins in a sample of tissue or body fluid may be detected via binding assays, wherein a binding partner for the marker protein is introduced into a sample suspected of containing the marker protein. In such an assay, the binding partner may be detectably labeled as, for example, with a radioisotopic or fluorescent marker. Labeled antibodies may be used in a similar manner in order to isolate selected marker proteins. Nucleic acids encoding marker proteins may be detected using nucleic acid probes having a sequence complementary to at least a portion of the sequence encoding the marker protein. Techniques such as PCR and, in particular, reverse transcriptase PCR, are useful means for isolating nucleic acids encoding a marker protein.

The examples which follow provide details of the isolation and characterization of breast cancer-associated proteins and methods for their use in the detection and treatment of breast cancer.

2. Detection of Breast Cancer

Once breast cancer-associated proteins have been identified, the proteins or nucleic acids encoding the proteins may be used as markers to determine whether an individual has breast cancer and, if so, suitable detection methods can be used to monitor the status of the disease.

Using the marker proteins or nucleic acids encoding the proteins, the skilled artisan can produce a variety of detection methods for detecting breast cancer in a human. The methods typically comprise the steps of detecting, by some means, the presence of one or more breast cancer-associated proteins or nucleic acids encoding such proteins in a tissue or body fluid sample of the human. The accuracy and/or reliability of the method for detecting breast cancer in a human may be further enhanced by detecting the presence of a plurality of breast cancer-associated proteins and/or nucleic acids in a preselected tissue or body fluid sample. The detection assays may comprise one or more of the protocols described hereinbelow.

2.A. Protein-Based Assays

The marker protein in a sample may be detected, for example, by combining the marker protein with a binding moiety capable of specifically binding the marker protein. The binding moiety may comprise, for example, a member of a ligand-receptor pair, i.e., a pair of molecules capable of having a specific binding interaction. The binding moiety may comprise, for example, a member of a specific binding pair, such as antibody-antigen, enzyme-substrate, nucleic acid-nucleic acid, protein-nucleic acid, protein-protein, or other specific binding pair known in the art. Binding proteins may be designed which have enhanced affinity for a target protein. Optionally, the binding moiety may be linked with a detectable label, such as an enzymatic, fluorescent, radioactive, phosphorescent or colored particle label. The labeled complex may be detected, e.g., visually or with the aid of a spectrophotometer or other detector.

Marker proteins may also be detected using gel electrophoresis techniques available in the art. In two-dimensional gel electrophoresis, the proteins are separated first in a pH gradient gel according to their isoelectric point. The resulting gel then is placed on a second polyacrylamide gel, and the proteins separated according to molecular weight (see, for example, O'Farrell (1975) *J. Biol. Chem.* 250: 4007–4021).

One or more marker proteins may be detected by first isolating proteins from a sample obtained from an individual suspected of having breast cancer, and then separating the proteins by two-dimensional gel electrophoresis to produce a characteristic two-dimensional gel electrophoresis pattern. The pattern may then be compared with a standard gel pattern produced by separating, under the same or similar conditions, proteins isolated from normal or cancer cells. The standard gel pattern may be stored in, and retrieved from an electronic database of electrophoresis patterns. The presence of a breast cancer-associated protein in the two-dimensional gel provides an indication that the sample being tested was taken from a person with breast cancer. As with the other detection assays described herein, the detection of two or more proteins, for example, in the two-dimensional gel electrophoresis pattern further enhances the accuracy of the assay. The presence of a plurality, e.g., two to five, breast cancer-associated proteins on the two-dimensional gel provides an even stronger indication of the presence of a breast cancer in the individual. The assay thus permits the early detection and treatment of breast cancer.

A breast cancer-associated marker protein may also be detected using any of a wide range of immunoassay techniques available in the art. For example, the skilled artisan may employ the sandwich immunoassay format to detect breast cancer in a body fluid sample. Alternatively, the skilled artisan may use conventional immuno-histochemical procedures for detecting the presence of the breast cancer-associated protein in a tissue sample using one or more labeled binding proteins.

In a sandwich immunoassay, two antibodies capable of binding the marker protein generally are used, e.g., one immobilized onto a solid support, and one free in solution and labeled with a detectable chemical compound. Examples of chemical labels that may be used for the second antibody include radioisotopes, fluorescent compounds, and enzymes or other molecules that generate colored or electrochemically active products when exposed to a reactant or enzyme substrate. When a sample containing the marker protein is placed in this system, the marker protein binds to both the immobilized antibody and the labeled antibody, to form a "sandwich" immune complex on the support's surface. The complexed protein is detected by washing away non-bound sample components and excess labeled antibody, and measuring the amount of labeled antibody complexed to protein on the support's surface. Alternatively, the antibody free in solution, which can be labeled with a chemical moiety, for example, a hapten, may be detected by a third antibody labeled with a detectable moiety which binds the free antibody or, for example, the hapten coupled thereto.

Both the sandwich immunoassay and tissue immunohistochemical procedures are highly specific and very sensitive, provided that labels with good limits of detection are used. A detailed review of immunological assay design, theory and protocols can be found in numerous texts in the art, including "*Practical Immunology*", Butt, W. R., ed., (1984) Marcel Dekker, New York and "*Antibodies, A Laboratory Approach*", Harlow et al. eds. (1988) Cold Spring Harbor Laboratory.

In general, immunoassay design considerations include preparation of antibodies (e.g., monoclonal or polyclonal antibodies) having sufficiently high binding specificity for the target protein to form a complex that can be distinguished reliably from products of nonspecific interactions. As used herein, the term "antibody" is understood to mean binding proteins, for example, antibodies or other proteins comprising an immunoglobulin variable region-like binding domain, having the appropriate binding affinities and specificities for the target protein. The higher the antibody binding specificity, the lower the target protein concentration that can be detected. As used herein, the terms "specific binding" or "binding specifically" are understood to mean that the binding moiety, for example, a binding protein has a binding affinity for the target protein of greater than about $10^5$ $M^{-1}$, more preferably greater than about $10^7$ $M^{-1}$.

Antibodies to an isolated target breast cancer-associated protein which are useful in assays for detecting a breast cancer in an individual may be generated using standard immunological procedures well known and described in the art. See, for example, *Practical Immunology*, Butt, N. R., ed., Marcel Dekker, NY, 1984. Briefly, an isolated target protein is used to raise antibodies in a xenogeneic host, such as a mouse, goat or other suitable mammal. The marker protein is combined with a suitable adjuvant capable of enhancing antibody production in the host, and is injected into the host, for example, by intraperitoneal administration.

Any adjuvant suitable for stimulating the host's immune response may be used. A commonly used adjuvant is Freund's complete adjuvant (an emulsion comprising killed and dried microbial cells and available from, for example, Calbiochem Corp., San Diego, or Gibco, Grand Island, N.Y.). Where multiple antigen injections are desired, the subsequent injections may comprise the antigen in combination with an incomplete adjuvant (e.g., cell-free emulsion). Polyclonal antibodies may be isolated from the antibody-producing host by extracting serum containing antibodies to the protein of interest. Monoclonal antibodies may be produced by isolating host cells that produce the desired antibody, fusing these cells with myeloma cells using standard procedures known in the immunology art, and screening for hybrid cells (hybridomas) that react specifically with the target protein and have the desired binding affinity.

Antibody binding domains also may be produced biosynthetically and the amino acid sequence of the binding domain manipulated to enhance binding affinity with a preferred epitope on the target protein. Specific antibody methodologies are well understood and described in the literature. A more detailed description of their preparation can be found, for example, in "*Practical Immunology*" (1984) (supra).

In addition, genetically engineered biosynthetic antibody binding sites, also known in the art as BABS or sFv's, may be used in the practice of the instant invention. Methods for making and using BABS comprising (i) non-covalently associated or disulfide bonded synthetic $V_H$ and $V_L$ dimers, (ii) covalently linked $V_H$-$V_L$ single chain binding sites, (iii) individual $V_H$ or $V_L$ domains, or (iv) single chain antibody binding sites are disclosed, for example, in U.S. Pat. Nos.: 5,091,513; 5,132,405; 4,704,692; and 4,946,778. Furthermore, BABS having requisite specificity for the breast cancer-associated proteins can be derived by phage antibody cloning from combinatorial gene libraries (see, for example, Clackson et al. (1991) *Nature* 352: 624–628). Briefly, phage each expressing on their coat surfaces BABS having immunoglobulin variable regions encoded by variable region gene sequences derived from mice pre-immunized with isolated breast cancer-associated proteins, or fragments thereof, are screened for binding activity against immobilized breast cancer-associated protein. Phage which bind to the immobilized breast cancer-associated proteins are harvested and the gene encoding the BABS is sequenced. The resulting nucleic acid sequences encoding the BABS of interest then may be expressed in conventional expression systems to produce the BABS protein.

The isolated breast cancer-associated protein also may be used for the development of diagnostic and other tissue evaluating kits and assays to monitor the level of the proteins in a tissue or fluid sample. For example, the kit may include antibodies or other specific binding proteins which bind specifically to the breast cancer-associated proteins and which permit the presence and/or concentration of the breast cancer-associated proteins to be detected and/or quantitated in a tissue or fluid sample.

Suitable kits for detecting breast cancer-associated proteins are contemplated to include, e.g., a receptacle or other means for capturing a sample to be evaluated, and means for detecting the presence and/or quantity in the sample of one or more of the breast cancer-associated proteins described herein. As used herein, "means for detecting" in one embodiment includes one or more antibodies specific for these proteins and means for detecting the binding of the antibodies to these proteins by, e.g., a standard sandwich immunoassay as described herein. Where the presence of a

2.B. Nucleic Acid-based Assays

The presence of a breast cancer in an individual also may be determined by detecting, in a tissue or body fluid sample, a nucleic acid molecule encoding a breast cancer-associated protein. Using methods well known to those of ordinary skill in the art, the breast cancer-associated proteins of the invention may be sequenced, and then, based on the determined sequence, oligonucleotide probes designed for screening a cDNA library (see, for example, Sambrook et al. (1989) supra).

A target nucleic acid molecule encoding a marker breast cancer-associated protein may be detected using a labeled binding moiety capable of specifically binding the target nucleic acid. The binding moiety may comprise, for example, a protein, a nucleic acid or a peptide nucleic acid. Additionally, a target nucleic acid, such as an mRNA encoding a breast cancer-associated protein, may be detected by conducting, for example, a Northern blot analysis using labeled oligonucleotides, e.g., nucleic acid fragments complementary to and capable of hybridizing specifically with at least a portion of a target nucleic acid.

More specifically, gene probes comprising complementary RNA or, preferably, DNA to the breast cancer-associated nucleotide sequences or mRNA sequences encoding breast cancer-associated proteins may be produced using established recombinant techniques or oligonucleotide synthesis. The probes hybridize with complementary nucleic acid sequences presented in the test specimen, and can provide exquisite specificity. A short, well-defined probe, coding for a single unique sequence is most precise and preferred. Larger probes are generally less specific. While an oligonucleotide of any length may hybridize to an mRNA transcript, oligonucleotides typically within the range of 8–100 nucleotides, preferably within the range of 15–50 nucleotides, are envisioned to be most useful in standard hybridization assays. Choices of probe length and sequence allow one to choose the degree of specificity desired. Hybridization is carried out at from 50° to 65° C. in a high salt buffer solution, formamide or other agents to set the degree of complementarity required. Furthermore, the state of the art is such that probes can be manufactured to recognize essentially any DNA or RNA sequence. For additional particulars, see, for example, *Guide to Molecular Techniques*, Berger et al., Methods of Enzymology, Vol. 152, 1987.

A wide variety of different labels coupled to the probes or antibodies may be employed in the assays. The labeled reagents may be provided in solution or coupled to an insoluble support, depending on the design of the assay. The various conjugates may be joined covalently or noncovalently, directly or indirectly. When bonded covalently, the particular linkage group will depend upon the nature of the two moieties to be bonded. A large number of linking groups and methods for linking are taught in the literature. Broadly, the labels may be divided into the following categories: chromogens; catalyzed reactions; chemiluminescence; radioactive labels; and colloidal-sized colored particles. The chromogens include compounds which absorb light in a distinctive range so that a color may be observed, or emit light when irradiated with light of a particular wavelength or wavelength range, e.g., fluorescers. Both enzymatic and nonenzymatic catalysts may be employed. In choosing an enzyme, there will be many considerations including the stability of the enzyme, whether it is normally present in samples of the type for which the assay is designed, the nature of the substrate, and the effect if any of conjugation on the enzyme's properties. Potentially useful enzyme labels include oxiodoreductases, transferases, hydrolases, lyases, isomerases, ligases, or synthetases. Interrelated enzyme systems may also be used. A chemiluminescent label involves a compound that becomes electronically excited by a chemical reaction and may then emit light that serves as a detectable signal or donates energy to a fluorescent acceptor. Radioactive labels include various radioisotopes found in common use such as the unstable forms of hydrogen, iodine, phosphorus or the like. Colloidal-sized colored particles involve material such as colloidal gold that, in aggregate, form a visually detectable distinctive spot corresponding to the site of a substance to be detected. Additional information on labeling technology is disclosed, for example, in U.S. Pat. No. 4,366,241.

A common method of in vitro labeling of nucleotide probes involves nick translation wherein the unlabeled DNA probe is nicked with an endonuclease to produce free 3'hydroxyl termini within either strand of the double-stranded fragment. Simultaneously, an exonuclease removes the nucleotide residue from the 5'phosphoryl side of the nick. The sequence of replacement nucleotides is determined by the sequence of the opposite strand of the duplex. Thus, if labeled nucleotides are supplied, DNA polymerase will fill in the nick with the labeled nucleotides. Using this well-known technique, up to 50% of the molecule can be labeled. For smaller probes, known methods involving 3'end labeling may be used. Furthermore, there are currently commercially available methods of labeling DNA with fluorescent molecules, catalysts, enzymes, or chemiluminescent materials. Biotin labeling kits are commercially available (Enzo Biochem Inc.) under the trademark Bio-Probe. This type of system permits the probe to be coupled to avidin which in turn is labeled with, for example, a fluorescent molecule, enzyme, antibody, etc. For further disclosure regarding probe construction and technology, see, for example, Sambrook et al., *Molecular Cloning, A Laboratory Manual* (Cold Spring Harbor, N.Y., 1982).

The oligonucleotide selected for hybridizing to the target nucleic acid, whether synthesized chemically or by recombinant DNA methodologies, is isolated and purified using standard techniques and then preferably labeled (e.g., with $^{35}S$ or $^{32}P$) using standard labeling protocols. A sample containing the target nucleic acid then is run on an electrophoresis gel, the dispersed nucleic acids transferred to a nitrocellulose filter and the labeled oligonucleotide exposed to the filter under stringent hybridizing conditions, e.g., 50% formamide, 5×SSPE, 2×Denhardt's solution, 0.1% SDS at 42° C., as described in Sambrook et al. (1989) supra. The filter may then be washed using 2×SSPE, 0.1% SDS at 68° C., and more preferably using 0.1×SSPE, 0.1% SDS at 68° C. Other useful procedures known in the art include solution hybridization, and dot and slot RNA hybridization. Optionally, the amount of the target nucleic acid present in a sample is then quantitated by measuring the radioactivity of hybridized fragments, using standard procedures known in the art.

In addition, oligonucleotides also may be used to identify other sequences encoding members of the target protein families. The methodology also may be used to identify genetic sequences associated with the nucleic acid sequences encoding the proteins described herein, e.g., to identify non-coding sequences lying upstream or downstream of the protein coding sequence, and which may play a functional role in expression of these genes. Additionally, binding assays may be conducted to identify and detect proteins capable of a specific binding interaction with a nucleic acid encoding a breast cancer-associated protein, which may be involved, e.g., in gene regulation or gene expression of the protein. In a further embodiment, the assays described herein may be used to identify and detect nucleic acid molecules comprising a sequence capable of recognizing and being specifically bound by a breast cancer-associated protein.

In addition, it is anticipated that using a combination of appropriate oligonucleotide primers, i.e., more than one primer, the skilled artisan may determine the level of expression of a target gene in vivo by standard polymerase chain reaction (PCR) procedures, for example, by quantitative PCR. Conventional PCR based assays are discussed, for example, in Innes et al (1990) "*PCR Protocols; A guide to methods and Applications*", Academic Press and Innes et al. (1995) "*PCR Strategies*" Academic Press, San Diego, Calif.

3. Identification of Proteins Which Interact In Vivo With Breast Cancer-associated Proteins In addition, it is contemplated that the skilled artisan, using procedures like those described hereinbelow, may identify other molecules which interact in vivo with the breast cancer-associated proteins described herein. Such molecules also may provide possible targets for chemotherapy.

By way of example, cDNA encoding proteins or peptides capable of interacting with breast cancer-associated proteins can be determined using a two-hybrid assay, as reported in Durfee et al. (1993) *Genes & Develop.* 7: 555–559. The principle of the two hybrid system is that noncovalent interaction of two proteins triggers a process (transcription) in which these proteins normally play no direct role, because of their covalent linkage to domains that function in this process. For example, in the two-hybrid assay, detectable expression of a reporter gene occurs when two fusion proteins, one comprising a DNA-binding domain and one comprising a transcription initiation domain, interact.

The skilled artisan can-use a host cell that contains one or more reporter genes, such as yeast strain Y153, reported in Durfee et al. (1993) supra. This strain carries two chromosomally located reporter genes whose expression is regulated by Gal4. A first reporter gene, is the *E. coli* lacZ gene under the control of the Gal4 promoter. A second reporter gene is the selectable HIS3 gene. Other useful reporter genes may include, for example, the luciferase gene, the LEU2 gene, and the GFP (Green Fluorescent Protein) gene.

Two sets of plasmids are used in the two hybrid system. One set of plasmids contains DNA encoding a Gal4 DNA-binding domain fused in frame to DNA encoding a breast cancer-associated protein. The other set of plasmids contain DNA encoding a Gal4 activation domain fused to portions of a human cDNA library constructed from human lymphocytes. Expression from the first set of plasmids results in a fusion protein comprising a Gal4 DNA-binding domain and a breast cancer-associated protein. Expression from the second set of plasmids produces a transcription activation protein fused to an expression product from the lymphocyte cDNA library. When the two plasmids are transformed into a Gal4-deficient host cell, such as the yeast Y153 cells described above, interaction of the Gal4 DNA binding domain and transcription activation domain occurs only if the breast cancer-associated protein fused to the DNA binding domain binds to a protein expressed from the lymphocyte cDNA library fused to the transcription activating domain. As a result of the protein-protein interaction between the breast cancer-associated protein and its in vivo binding partner detectable levels of reporter gene expression occur.

In addition to identifying molecules which interact in vivo with the breast cancer-associated proteins, the skilled artisan may also screen for molecules, for example, small molecules which alter or inhibit specific interaction between a breast cancer-associated protein and its in vivo binding partner.

For example, a host cell can be transfected with DNA encoding a suitable DNA binding domain/breast cancer-associated protein hybrid and a translation activation domain/putative breast cancer-associated protein binding partner, as disclosed above. The host cell also contains a suitable reporter gene in operative association with a cis-acting transcription activation element that is recognized by the transcription factor DNA binding domain. The level of reporter gene expressed in the system is assayed. Then, the host cell is exposed to a candidate molecule and the level of reporter gene expression is detected. A reduction in reporter gene expression is indicative of the candidate's ability to interfere with complex formation or stability with respect to the breast cancer-associated protein and its in vivo binding partner. As a control, the candidate molecule's ability to interfere with other, unrelated protein-protein complexes is also tested. Molecules capable of specifically interfering with a breast cancer-associated protein/binding partner interaction, but not other protein-protein interactions, are identified as candidates for production and further analysis. Once a potential candidate has been identified, its efficacy in modulating cell cycling and cell replication can be assayed in a standard cell cycle model system.

Candidate molecules can be produced as described hereinbelow. For example, DNA encoding the candidate molecules can be inserted, using conventional techniques well described in the art (see, for example, Sambrook (1989) supra) into any of a variety of expression vectors and transfected into an appropriate host cell to produce recombinant proteins, including both full length and truncated forms. Useful host cells include *E. coli, Saccharomyces cerevisiae, Pichia pastoris*, the insect/baculovirus cell system, myeloma cells, and various other mammalian cells. The full length forms of such proteins are preferably expressed in mammalian cells, as disclosed herein. The nucleotide sequences also preferably include a sequence for targeting the translated sequence to the nucleus, using, for example, a sequence encoding the eight amino acid nucleus targeting sequence of the large T antigen, which is well characterized in the art. The vector can additionally include various sequences to promote correct expression of the recombinant protein, including transcription promoter and termination sequences, enhancer sequences, preferred ribosome binding site sequences, preferred mRNA leader sequences, preferred protein processing sequences, preferred signal sequences for protein secretion, and the like. The DNA sequence encoding the gene of interest can also be manipulated to remove potentially inhibiting sequences or to minimize unwanted secondary structure formation. As will be appreciated by the practitioner in the art, the recombinant protein can also be expressed as a fusion protein.

After translation, the protein can be purified from the cells themselves or recovered from the culture medium. The DNA can also include sequences which aid in expression and/or purification of the recombinant protein. The DNA can be expressed directly or can be expressed as part of a fusion protein having a readily cleavable fusion junction.

The DNA may also be expressed in a suitable mammalian host. Useful hosts include fibroblast 3T3 cells, (e.g., NIH 3T3, from CRL 1658) COS (simian kidney ATCC, CRL-1650) or CHO (Chinese hamster ovary) cells (e.g., CHO-DXB11, from Chasin (1980) *Proc. Nat'l. Acad. Sci. USA*

77:4216–4222), mink-lung epithelial cells (MV1Lu), human foreskin fibroblast cells, human glioblastoma cells, and teratocarcinoma cells. Other useful eukaryotic cell systems include yeast cells, the insect/baculovirus system or myeloma cells.

In order to express a candidate molecule, the DNA is subcloned into an insertion site of a suitable, commercially available vector along with suitable promoter/enhancer sequences and 3' termination sequences. Useful promoter/ enhancer sequence combinations include the CMV promoter (human cytomegalovirus (MIE) promoter) present, for example, on pCDM8, as well as the mammary tumor virus promoter (MMTV) boosted by the Rous sarcoma virus LTR enhancer sequence (e.g., from Clontech, Inc., Palo Alto). A useful inducable promoter includes, for example, a $Zn^{2+}$-inducible promoter, such as the $Zn^{2+}$ metallothionein promoter (Wrana et al. (1992) Cell 71: 1003–1014). Other inducible promoters are well known in the art and can be used with similar success. Expression also can be further enhanced using trans-activating enhancer sequences. The plasmid also preferably contains an amplifiable marker, such as DHFR under suitable promoter control, e.g., SV40 early promoter (ATCC #37148). Transfection, cell culturing, gene amplification and protein expression conditions are standard conditions, well known in the art, such as are described, for example in Ausubel et al., ed., (1989) "*Current Protocols in Molecular Biology*", John Wiley & Sons, NY. Briefly, transfected cells are cultured in medium containing 5–10% dialyzed fetal calf serum (dFCS), and stably transfected high expression cell lines obtained by amplification and subcloning and evaluated by standard Western and Northern blot analysis. Southern blots also can be used to assess the state of integrated sequences and the extent of their copy number amplification.

The expressed candidate protein is then purified using standard procedures. A currently preferred methodology uses an affinity column, such as a ligand affinity column or an antibody affinity column. The column then is washed, and the candidate molecules selectively eluted in a gradient of increasing ionic strength, changes in pH, or addition of mild detergent. It is appreciated that in addition to the candidate molecules which bind to the breast cancer-associated proteins, the breast cancer associated proteins themselves may likewise be produced using such recombinant DNA technologies.

4. Breast Cancer Therapy and Methods for Monitoring Therapy

The skilled artisan, after identification of breast cancer-associated proteins and proteins which interact with the breast cancer-associated proteins, can develop a variety of therapies for treating breast cancer. Because the marker proteins described herein are present at detectably higher levels in breast cancer cells relative to normal breast cells, the skilled artisan may employ, for example, the marker proteins and/or nucleic acids encoding the marker proteins as target molecules for a cancer chemotherapy.

4.A. Anti-sense-based Therapeutics

A particularly useful cancer therapeutic envisioned is an oligonucleotide or peptide nucleic acid sequence complementary and capable of hybridizing under physiological conditions to part, or all, of the gene encoding the marker protein or to part, or all, of the transcript encoding the marker protein thereby to reduce or inhibit transcription and/or translation of the marker protein gene. Alternatively, the same technologies may be applied to reduce or inhibit transcription and/or translation of the proteins which interact with the breast cancer-associated proteins.

Anti-sense oligonucleotides have been used extensively to inhibit gene expression in normal and abnormal cells. See, for example, Stein et al. (1988) *Cancer Res.* 48: 2659–2668, for a pertinent review of anti-sense theory and established protocols. In addition, the synthesis and use of peptide nucleic acids as anti-sense-based therapeutics are described in PCT publications PCT/EP92/01219 published Nov. 26, 1992, PCT/US92/10921 published Jun. 24, 1993, and PCT/ US94/013523 published Jun. 1, 1995. Accordingly, the anti-sense-based therapeutics may be used as part of chemotherapy, either alone or in combination with other therapies.

Anti-sense oligonucleotide and peptide nucleic acid sequences are capable of hybridizing to a gene and/or mRNA transcript and, therefore, may be used to inhibit transcription and/or translation of the protein described herein. It is appreciated, however, that oligoribonucleotide sequences generally are more susceptible to enzymatic attack by ribonucleases than are deoxyribonucleotide sequences. Hence, oligodeoxyribonucleotides are preferred over oligoribonucleotides for in vivo therapeutic use. It is appreciated that the peptide nucleic acid sequences, unlike regular nucleic acid sequences, are not susceptible to nuclease degradation and, therefore, are likely to have greater longevity in vivo. Furthermore, it is appreciated that peptide nucleic acid sequences bind complementary single stranded DNA and RNA strands more strongly than corresponding DNA sequences (see, for example, PCT/EP92/ 20702 published Nov. 26, 1992). Accordingly, peptide nucleic acid sequences are preferred for in vivo therapeutic use.

Therapeutically useful anti-sense oligonucleotides or peptide nucleic acid sequences may be synthesized by any of the known chemical oligonucleotide and peptide nucleic acid synthesis methodologies well known and thoroughly described in the art. Alternatively, a sequence complementary to part or all of the natural mRNA sequence may be generated using standard recombinant DNA technologies.

Because the complete nucleotide sequence encoding the entire marker protein as well as additional 5' and 3' untranslated sequences are known for each of the marker proteins and/or can be determined readily using techniques well known in the art, anti-sense oligonucleotides or peptide nucleic acids which hybridize with any portion of the mRNA transcript or non-coding sequences may be prepared using conventional oligonucleotide and peptide nucleic acid synthesis methodologies.

Oligonucleotides complementary to, and hybridizable with, any portion of the mRNA transcripts encoding the marker proteins are, in principle, effective for inhibiting translation of the target proteins as described herein. For example, as described in U.S. Pat. No. 5,098,890, issued Mar. 24, 1992, oligonucleotides complementary to mRNA at or near the translation initiation codon site may be used to inhibit translation. Moreover, it has been suggested that sequences that are too distant in the 3' direction from the translation initiation site may be less effective in hybridizing the mRNA transcripts because of potential ribosomal "read-through", a phenomenon whereby the ribosome is postulated to unravel the anti-sense/sense duplex to permit translation of the message.

A variety of sequence lengths of oligonucleotide or peptide nucleic acid may be used to hybridize to mRNA transcripts. However, very short sequences (e.g., sequences containing less than 8–15 nucleobases) may bind with less specificity. Moreover, for in vivo use, short oligonucleotide sequences may be particularly susceptible to enzymatic degradation. Peptide nucleic acids, as mentioned above, likely are resistant to nuclease degradation. Where oligonucleotide and peptide nucleic acid sequences are to be provided directly to the cells, very long sequences may be less effective at inhibition because of decreased uptake by the target cell. Accordingly, where the oligonucleotide or peptide nucleic acid is to be provided directly to target cells, oligonucleotide and/or peptide nucleic acid sequences containing about 8–50 nucleobases, and more preferably 15–30 nucleobases, are envisioned to be most advantageous.

An alternative means for providing anti-sense oligonucleotide sequences to a target cell is gene therapy where, for example, a DNA sequence, preferably as part of a vector and associated with a promoter, is expressed constitutively inside the target cell. Oeller et al. (Oeller et al. (1992) *Science* 254: 437–539) describe the in vivo inhibition of the ACC synthase enzyme using a constitutively expressible DNA sequence encoding an anti-sense sequence to the full length ACC synthase transcript. Accordingly, where the anti-sense oligonucleotide sequences are provided to a target cell indirectly, for example, as part of an expressible gene sequence to be expressed within the cell, longer oligonucleotide sequences, including sequences complementary to substantially all the protein coding sequence, may be used to advantage.

Finally, therapeutically useful oligonucleotide sequences envisioned also include not only native oligomers composed of naturally occurring nucleotides, but also those comprising modified nucleotides, for example, to improve stability and lipid solubility and thereby enhance cellular uptake. For example, it is known that enhanced lipid solubility and/or resistance to nuclease digestion results by substituting a methyl group or sulfur atom for a phosphate oxygen in the internucleotide phosphodiester linkage. Phosphorothioates ("S-oligonucleotides" wherein a phosphate oxygen is replaced by a sulfur atom), in particular, are stable to nuclease cleavage, are soluble in lipids, and are preferred, particularly for direct oligonucleotide administration. S-oligonucleotides may be synthesized chemically using conventional synthesis methodologies well known and thoroughly described in the art.

Preferred synthetic internucleoside linkages include phosphorothioates, alkylphosphonates, phosphorodithioates, phosphate esters, alkylphosphonothioates, phosphoramidates, carbamates, carbonates, phosphate triesters, acetamidate, and carboxymethyl esters. Furthermore, one or more of the 5'-3' phosphate group may be covalently joined to a low molecular weight (e.g., 15–500 Da) organic group, including, for example, lower alkyl chains or aliphatic groups (e.g., methyl, ethyl, propyl, butyl), substituted alkyl and aliphatic groups (e.g., aminoethyl, aminopropyl, aminohydroxyethyl, aminohydroxypropyl), small saccharides or glycosyl groups. Other low molecular weight organic modifications include additions to the internucleoside phosphate linkages such as cholesteryl or diamine compounds with varying numbers of carbon residues between the amino groups and terminal ribose. Oligonucleotides with these linkages or with other modifications can be prepared using methods well known in the art (see, for example, U.S. Pat. No. 5,149,798).

Suitable oligonucleotide and/or peptide nucleic acid sequences which inhibit transcription and/or translation of the marker proteins can be identified using standard in vivo assays well characterized in the art. Preferably, a range of doses is used to determine effective concentrations for inhibition as well as specificity of hybridization. For example, in the cases of an oligonucleotide, a dose range of 0–100 $\mu$g oligonucleotide/ml may be assayed. Further, the oligonucleotides may be provided to the cells in a single transfection, or as part of a series of transfections. Anti-sense efficacy may be determined by assaying a change in cell proliferation over time following transfection, using standard cell counting methodology and/or by assaying for reduced expression of marker protein, e.g., by immunofluorescence. Alternatively, the ability of cells to take up and use thymidine is another standard means of assaying for cell division and may be used here, e.g., using $^3$H-thymidine. Effective anti-sense inhibition should inhibit cell division sufficiently to reduce thymidine uptake, inhibit cell proliferation, and/or reduce detectable levels of marker proteins.

It is anticipated that therapeutically effective oligonucleotide or peptide nucleic acid concentrations may vary according to the nature and extent of the neoplasm, the particular nucleobase sequence used, the relative sensitivity of the neoplasm to the oligonucleotide or peptide nucleic acid sequence, and other factors. Useful ranges for a given cell type and oligonucleotide and/or peptide nucleic acid may be determined by performing standard dose range experiments. Dose range experiments also may be performed to assess toxicity levels for normal and malignant cells. It is contemplated that useful concentrations may range from about 1 to 100 $\mu$g/ml per $10^5$ cells.

For in vivo use, the anti-sense oligonucleotide or peptide nucleic acid sequences may be combined with a pharmaceutically acceptable carrier, such as a suitable liquid vehicle or excipient, and optionally an auxiliary additive or additives. Liquid vehicles and excipients are conventional and are available commercially. Illustrative thereof are distilled water, physiological saline, aqueous solutions of dextrose, and the like. For in vivo cancer therapies, the anti-sense sequences preferably can be provided directly to malignant cells, for example, by injection directly into the tumor. Alternatively, the oligonucleotide or peptide nucleic acid may be administered systemically, provided that the anti-sense sequence is associated with means for directing the sequences to the target malignant cells.

In addition to administration with conventional carriers, the anti-sense oligonucleotide or peptide nucleic acid sequences may be administered by a variety of specialized oligonucleotide delivery techniques. For example, oligonucleotides may be encapsulated in liposomes, as described in Mannino et al. (1988) *BioTechnology* 6: 682, and Felgner et al. (1989) *Bethesda Res. Lab. Focus* 11:21. Lipids useful in producing liposomal formulations include, without limitation, monoglycerides, diglycerides, sulfatides, lysolecithin, phospholipids, saponin, bile acids, and the like. Preparation of such liposomal formulations is within the level of skill in the art (see, for example, in U.S. Pat. No. 4,235,871; U.S. Pat. No. 4,501,728; U.S. Pat. No. 4,837,028; and U.S. Pat. No. 4,737,323). The pharmaceutical composition of the invention may further include compounds such as cyclodextrins and the like which enhance delivery of oligonucleotides into cells. When the composition is not administered systemically but, rather, is injected at the site of the target cells, cationic detergents (e.g. Lipofectin) may be added to enhance uptake. In addition, reconstituted virus envelopes have been successfully used to deliver RNA and DNA to cells (see, for example, Arad et al. (1986) *Biochem. Biophy. Acta.* 859: 88–94).

For therapeutic use in vivo, the anti-sense oligonucleotide and/or peptide nucleic acid sequences are administered to the individual in a therapeutically effective amount, for example, an amount sufficient to reduce or inhibit target protein expression in malignant cells. The actual dosage administered may take into account whether the nature of the treatment is prophylactic or therapeutic in nature, the age, weight, health of the patient, the route of administration, the size and nature of the malignancy, as well as other factors. The daily dosage may range from about 0.01 to 1,000 mg per day. Greater or lesser amounts of oligonucleotide or peptide nucleic acid sequences may be administered, as required. As will be appreciated by those skilled in the medical art, particularly the chemotherapeutic art, appropriate dose ranges for in vivo administration would be routine experimentation for a clinician. As a preliminary guideline, effective concentrations for in vitro inhibition of the target molecule may be determined first.

4.B. Binding Protein-based Therapeutics.

As mentioned above, a cancer marker protein or a protein that interacts with the cancer marker protein may be used as a target for chemotherapy. For example, a binding protein designed to bind the marker protein essentially irreversibly can be provided to the malignant cells, for example, by association with a ligand specific for the cell and known to be absorbed by the cell. Means for targeting molecules to particular cells and cell types are well described in the chemotherapeutic art.

Binding proteins may be obtained and tested using technologies well known in the art. For example, the binding portions of antibodies may be used to advantage. It is contemplated, however, that intact antibodies or BABS that have preferably been humanized may be used in the practice of the invention. As used herein, the term "humanized" is understood to mean a process whereby the framework region sequences of a non-human immunoglobulin variable region are replaced by corresponding human framework sequences. Accordingly, it is contemplated that such humanized binding proteins will elicit a weaker immune response than their unhumanized counterparts. Particularly useful are binding proteins identified with high affinity for the target protein, e.g., greater than about $10^9$ $M^{-1}$. Alternatively, DNA encoding the binding protein may be provided to the target cell as part of an expressible gene to be expressed within the cell following the procedures used for gene therapy protocols well described in the art. See, for example, U.S. Pat. No. 4,497,796, and "Gene Transfer", Vijay R. Baichwal, ed., (1986). It is anticipated that, once bound by binding protein, the target protein will be inactivated or its biological activity reduced thereby inhibiting or retarding cell division.

As described above, suitable binding proteins for in vivo use may be combined with a suitable pharmaceutically-acceptable carrier, such as physiological saline or other useful carriers well characterized in the medical art. The pharmaceutical compositions may be provided directly to malignant cells, for example, by direct injection, or may be provided systemically, provided the binding protein is associated with means for targeting the protein to target cells. Finally, suitable dose ranges and cell toxicity levels may be assessed using standard dose range experiments. Therapeutically-effective concentrations may range from about 0.01 to about 1,000 mg per day. As described above, actual dosages administered may vary depending, for example, on the nature of the malignancy, the age, weight and health of the individual, as well as other factors.

4.C Small Molecule-based Therapeutics.

After having isolated breast cancer-associated proteins, the skilled artisan can, using methodologies well known in the art, screen small molecule libraries (either peptide or non-peptide based libraries) to identify candidate molecules that reduce or inhibit the biological function of the breast cancer-associated proteins. The small molecules preferably accomplish this function by reducing the in vivo expression of the target molecule, or by interacting with the target molecule thereby to inhibit either the biological activity of the target molecule or an interaction between the target molecule and its in vivo binding partner.

It is contemplated that, once the candidate small molecules have been elucidated, the skilled artisan may enhance the efficacy of the small molecule using rational drug design methodologies well known in the art. Alternatively, the skilled artisan may use a variety of computer programs which assist the skilled artisan to develop quantitative structure activity relationships (QSAR) which further to assist the design of additional candidate molecules de novo. Once identified, the small molecules may be produced in commercial quantities and subjected to the appropriate safety and efficacy studies.

It is contemplated that the screening assays may be automated thereby facilitating the screening of a large number of small molecules at the same time. Such automation procedures are within the level of skill in the art of drug screening and, therefore, are not discussed herein.

Candidate peptide-based small molecules may be produced by expression of an appropriate nucleic acid sequence in a host cell or using synthetic organic chemistries. Similarly, non-peptidyl-based small molecules may be produced using conventional synthetic organic chemistries well known in the art.

As described above, for in vivo use, the identified small molecules may be combined with a suitable pharmaceutically acceptable carrier, such as physiological-saline or other useful carriers well characterized in the medical art. The pharmaceutical compositions may be provided directly to malignant cells, for example, by direct injection, or may be provided systemically, provided the binding protein is associated with means for targeting the protein to target cells. Finally, suitable dose ranges and cell toxicity levels may be assessed using standard dose range experiments. As described above, actual dosages administered may vary depending, for example, on the nature of the malignancy, the age, weight and health of the individual, as well as other factors.

4.D. Methods for Monitoring the Status of Breast Cancer in an Individual

The progression of the breast cancer or the therapeutic efficacy of chemotherapy may be measured using procedures well known in the art. For example, the efficacy of a particular chemotherapeutic agent can be determined by measuring the amount of a breast cancer-associated protein released from breast cancer cells undergoing cell death. As reported in U.S. Pat. Nos. 5,840,503 and 5,965,376, soluble nuclear matrix proteins and fragments thereof are released by cells upon cell death. Such soluble nuclear matrix proteins can be quantitated in a body fluid and used to monitor the degree or rate of cell death in a tissue. Similarly, the levels of one or more breast cancer-associated proteins could be used as an indication of the status of breast cancer in the individual.

For example, the concentration of a breast cancer-associated protein or a fragment thereof released from cells is compared to standards from healthy, untreated tissue. Fluid samples are collected at discrete intervals during treatment and compared to the standard. It is contemplated that changes in the level of the breast cancer-associated protein, for example, will be indicative of the efficacy of treatment (that is, the rate of cancer cell death). It is contemplated that the release of soluble, breast cancer-associated proteins can be measured in blood, plasma, urine, sputum, vaginal secretion, and breast exudate and other body fluids.

Where the assay is used to monitor tissue viability or progression of breast cancer, the step of detecting the presence and abundance of the marker protein or its transcript in samples of interest is repeated at intervals and these values then are compared, the changes in the detected concentrations reflecting changes in the status of the tissue. For example, an increase in the level of one or more breast cancer-associated proteins may correlate with progression of the breast cancer. Where the assay is used to evaluate the efficacy of a therapy, the monitoring steps occur following administration of the therapeutic agent or procedure (e.g., following administration of a chemotherapeutic agent or following radiation treatment). Similarly, a decrease in the level of breast cancer-associated proteins may correlate with a regression of the breast cancer.

Thus, breast cancer may be identified by the presence of breast cancer-associated proteins as taught herein. Once identified, the breast cancer may be treated using compounds that reduce in vivo the expression and/or biological activity of the breast cancer-associated proteins. Furthermore, the methods provided herein can be used to monitor the progression and/or treatment of the disease. The following non-limiting examples provide details of the isolation and characterization of breast cancer-associated proteins and methods for their use in the detection of breast cancer.

EXAMPLE 1

Identification of Breast Cancer Markers

To identify markers for breast cancer, the sera of individuals with breast cancer were compared to the sera of normal individuals by surface-enhanced laser desorption and ionization (SELDI) mass spectrometry. Briefly, 0.5 mL aliquots of sera harvested from the individuals were thawed. Then, 1 $\mu$L of a 1 mg/mL solution of soybean trypsin inhibitor (SBTI) and 1 $\mu$L of a 1 mg/mL solution of leupeptin were added to each aliquot. To remove lipids, 350 $\mu$L of 1,1,2-trifluorotrichloroethane was added to each sample. The samples then were vortexed for five minutes and centrifuged in a microcentrifuge for five minutes at 4° C. The resulting supernatants were applied a 1 mL column of agarose coupled to protein G (Hitrap Protein G column, Pharmacia and Upjohn, Peapack, N.J.) to remove immunoglobulin proteins. The column then was rinsed with 3 mL of 50 mM sodium phosphate, pH 7.0, with SBTI and leupeptin ("binding buffer"), and the resulting flowthrough applied directly to a 5 mL column of 6% Sepharose coupled to Cibacron blue (Hitrap blue column, Pharmacia and Upjohn, Peapack, N.J.) to remove albumin proteins. The Hitrap blue column was rinsed with 20 mL of binding buffer. The resulting flowthrough was concentrated using four centrifugation-based concentrators with a 10 kD cutoff (Centricon 10, Millipore Corporation, Bedford, Mass.) to a final volume of about 0.7 mL.

The resulting serum (substantially free of immunoglobulin and albumin) was subdivided into twelve fractions containing approximately equal amounts of protein by ion exchange chromatography. Specifically, the serum was applied to a Mono Q (Pharmacia and Upjohn, Peapack, N.J.) ion exchange column (a strong anion exchanger with quarternary ammonium groups) in 50 mM sodium phosphate buffer, pH 7.0 and proteins were eluted from the column by increasing the concentration of sodium chloride in a stepwise manner. Thus, the serum was divided into twelve fractions based on the concentration of sodium chloride used for elution. These fractions accordingly were designated flow through, 25 mM, 50 mM, 75 mM, 100 mM, 125 mM, 150 mM, 200 mM, 250 mM, 300 mM, 400 mM, and 2M sodium chloride. After elution, each fraction was concentrated to approximately 100 $\mu$g/mL and buffer exchanged into binding buffer.

Then 4–10 $\mu$L from each of the twelve fractions were applied and allowed to bind to each of four SELDI chip surfaces, each surface holding up to eight samples. The intended location of each sample on the chip was demarcated with a circle drawn using a hydrophobic marker like those used in Pap smears. The SELDI chips used herein were purchased from Ciphergen Biosystems, Inc., Palo Alto, Calif., and used as described below.

For copper or nickel surfaces, a chip containing ethylenediaminetriacetic acid moieties (IMAC, Ciphergen Biosystems, Inc., Palo Alto, Calif.) was pretreated with two five-minute applications of five $\mu$L of a copper salt or nickel salt solution, and washed with deionized water. After a five-minute treatment with five $\mu$L of binding buffer, two to three microliters of sample were applied to the surface for thirty to sixty minutes. Another two to three microliters of sample were then applied for an additional thirty to sixty minutes. The chips then were washed twice with binding buffer to remove unbound proteins. 0.5 $\mu$L of sinapinic acid (12.5 mg/mL) was added twice and allowed to dry each time. The presence of sinapinic acid enhances the vaporization and ionization of the bound proteins upon mass spectrometry.

For chip surfaces containing carboxyl moieties (WCX-2, Ciphergen Biosystems, Inc., Palo Alto, Calif.), before use of the hydrophobic pen, the surface was washed with 10 mM HCl for thirty minutes and rinsed five times with deionized water. After use of the pen, the surface was washed five times with five $\mu$L of binding buffer and once with deionized water. Two to three $\mu$L of sample were applied in two applications of thirty to sixty minutes each. The surface was washed twice with 5 $\mu$L of binding buffer, and 0.5 $\mu$L of sinapinic acid were applied twice.

For chip surfaces containing quarternary ammonium moieties (SAX-2, Ciphergen Biosystems, Inc., Palo Alto, Calif.), after use of the pen, the surface was washed five times with five $\mu$L of binding buffer and once with deionized water. Application of sample, washing, and application of sinapinic acid were done as described above.

The chips then were subjected to mass spectrometry utilizing a Ciphergen SELDI PBS One (Ciphergen Biosystems, Inc., Palo Alto, Calif.) running the software program "SELDI v. 2.0". For all chips, "high mass" was set to 200,000 Daltons, "starting detector sensitivity" was set to 9 (from a range of 1–10, with 10 being the highest sensitivity), NDF (neutral density filter) was set to "OUT"s, data acquisition method was set to "Seldi Quantitation", SELDI acquisition parameters were set to 20, with increments of 5, and warming with two shots at intensity 50 (out of 100) was included. For IMAC chips, mass was optimized from 3000 Daltons to 3001 Daltons, starting laser intensity was set to 80 (out of 100), and transients set to 5 (i.e., 5 laser shots per site). Peaks were identified automatically by the computer. For WCX-2 chips, mass was optimized from 3,000 Daltons to 50,000 Daltons, starting laser intensity was set to 80, and transients set to 8. Peaks were identified automatically by the computer. For SAX-2 chips, mass was optimized from 3,000 Daltons to 50,000 Daltons, starting laser intensity was set to 85, and transients set to 8. Peaks were identified automatically by the computer.

Ten serum samples (five from normal individuals and five from individuals with breast cancer) were analyzed by mass spectrometry to identify the proteins present in the sixty fractions described above. The resulting peaks in the mass spectrometry trace were compared to identify those peaks present in the serum samples from individuals with breast cancer but not present in the normal samples. If peaks in different samples had a mass difference of no more than one percent, the peaks were presumed to be the same. Eleven mass spectrometry peaks ranging in size from just over 11,000 Da to approximately 103,000 Da were identified as present in all five serum samples from individuals with breast cancer and in none of the samples from normal individuals. The presence or absence of these peaks was then determined for an additional thirty serum samples (fifteen from normal individuals and fifteen from individuals with breast cancer). Seven other peaks that were present in four of the original five breast cancer serum samples, but not in any of the normal samples, were also analyzed because they were present in the same fraction and on the same SELDI surface as one or more of the eleven peaks already under evaluation. Of the eighteen peaks studied, fifteen were present in fifteen or more of the twenty breast cancer serum samples, but absent from 15 or more of the normal serum samples.

The results of the foregoing analyses are summarized in Table 1. The masses listed in the presumed accurate to within one percent.

TABLE 1

| Mass (Da) | Mono Q fraction (mM) sodium chloride) | SELDI chip surface used | Number of positive samples from individuals with breast cancer | Number of positive samples from individuals without breast cancer |
|---|---|---|---|---|
| 16210 | 0 (flow through) | Nickel | 17 | 1 |
| 17188 | 25 mM | WCX-2 | 17 | 2 |
| 30183 | 25 mM | WCX-2 | 15 | 3 |
| 34664 | 25 mM | WCX-2 | 16 | 4 |
| 20050 | 50 mM | Nickel | 19 | 0 |
| 28258 | 50 mM | Nickel | 20 | 0 |
| 24170 | 50 mM | Nickel | 17 | 0 |
| 35393 | 50 mM | Nickel | 17 | 3 |
| 34908 | 50 mM | WCX-2 | 16 | 2 |
| 70908 | 100 mM | WCX-2 | 20 | 0 |
| 17840 | 100 mM | WCX-2 | 18 | 2 |
| 11709 | 150 mM | SAX-2 | 20 | 0 |
| 42354 | 200 mM | Nickel | 17 | 0 |
| 56280 | 200 mM | Nickel | 16 | 0 |
| 34517 | 400 mM | Copper | 18 | 1 |

EXAMPLE 2

Sequencing of Breast Cancer Marker Proteins

Breast cancer-associated proteins based upon the biochemical and mass spectrometry data provided above may be better characterized using well-known techniques. For example, samples of the serum can be fractionated using, for example, column chromatography and/or electrophoresis, to produce purified protein samples corresponding to each of the proteins identified in Table 1. The sequences of the isolated proteins can then be determined using conventional peptide sequencing methodologies (see Examples 5 and 6).

It is appreciated that the skilled artisan, in view of the foregoing disclosure, would be able to produce an antibody directed against any breast cancer-associated protein identified by the methods described herein. Moreover, the skilled artisan, in view of the foregoing disclosure, would be able to produce nucleic acid sequences that encode the fragments described above, as well as nucleic acid sequences complementary thereto. In addition, the skilled artisan using conventional recombinant DNA methodologies, for example, by screening a cDNA library with such a nucleic acid sequence, would be able to isolate full length nucleic acid sequences encoding target breast cancer-associated proteins. Such full length nucleic acid sequences, or fragments thereof, may be used to generate nucleic acid-based detection systems or therapeutics.

EXAMPLE 3

Production of Antibodies Which Bind Specifically to Breast Cancer-associated Proteins Once identified, a breast cancer-associated protein may be detected in a tissue or body fluid sample using numerous binding assays that are well known to those of ordinary skill in the art. For example, as discussed above, a breast cancer-associated protein may be detected in either a tissue or body fluid sample using an antibody, for example, a monoclonal antibody, which binds specifically to an epitope disposed upon the breast cancer-associated protein. In such detection systems, the antibody preferably is labeled with a detectable moiety.

Provided below is an exemplary protocol for the production of an anti-breast cancer-associated monoclonal antibody. Other protocols also are envisioned. Accordingly, the particular method of producing antibodies to target proteins is not envisioned to be an aspect of the invention.

Balb/c by J mice (Jackson Laboratory, Bar Harbor, Me.) are injected intraperitoneally with the target protein every 2 weeks until the immunized mice obtain the appropriate serum titer. Thereafter, the mice are injected with 3 consecutive intravenous boosts. Freund's complete adjuvant (Gibco, Grand Island) is used in the first injection, incomplete Freund's in the second injection; and saline is used for subsequent intravenous injections. The animal then is sacrificed and its spleen removed. Spleen cells (or lymph node cells) then are fused with a mouse myeloma line, e.g., using the method of Kohler et al. (1975) Nature 256: 495. Hybridomas producing antibodies that react with the target proteins then are cloned and grown as ascites. Hybridomas are screened by reactivity to the immunogen in any desirable assay. Detailed descriptions of screening protocols, ascites production and immunoassays also are disclosed in PCT/US92/09220, published May 13, 1993.

EXAMPLE 4

Antibody-based Assay for Detecting Breast Cancer in an Individual

The following assay has been developed for tissue samples; however, it is contemplated that similar assays for testing fluid samples may be developed without undue experimentation. A typical assay may employ a commercial immunodetection kit, for example, the ABC Elite Kit from Vector Laboratories, Inc.

A biopsy sample is removed from the patient under investigation in accordance with the appropriate medical guidelines. The sample then is applied to a glass microscope slide and the sample fixed in cold acetone for 10 minutes. Then, the slide is rinsed in distilled water and pretreated with a hydrogen peroxide containing solution (2 mL 30% $H_2O_2$ and 30 mL cold methanol). The slide then is rinsed in a Buffer A comprising Tris Buffered Saline (TBS) with 0.1% Tween and 0.1% Brij. A mouse anti-breast cancer-associated protein monoclonal antibody in Buffer A is added to the slide and the slide then incubated for one hour at room temperature. The slide then is washed with Buffer A, and a secondary antibody (ABC Elite Kit, Vector Labs, Inc) in Buffer A is added to the slide. The slide then is incubated for 15 minutes at 37° C. in a humidity chamber. The slides are washed again with Buffer A, and the ABC reagent (ABC Elite Kit, Vector Labs, Inc.) is then added to the slide for amplification of the signal. The slide is then incubated for a further 15 minutes at 37° C. in the humidity chamber.

The slide then is washed in distilled water, and a diaminobenzedine (DAB) substrate added to the slide for 4–5 minutes. The slide then is rinsed with distilled water, counterstained with hematoxylin, rinsed with 95% ethanol, rinsed with 100% ethanol, and then rinsed with xylene. A cover slip is then applied to the slide and the result observed by light microscopy.

EXAMPLE 5

Purification and Characterization of 28.3 kD Breast Cancer Protein

The 28.3 kD breast cancer protein identified in Example 1 was isolated and further characterized as follows.

Approximately 30 mL of serum (combined from multiple breast cancer patients) was depleted of immunoglobulin G and serum albumin using Protein G chromatography and Cibacron Blue agarose chromatography, respectively, using standard methodologies such as those described in Example 1. The albumin and immunoglobulin depleted serum then was fractionated by Mono Q ion-exchange affinity chromatography. Briefly, the serum proteins were applied to a 5 mL Mono Q column (Pharmacia and Upjohn, Peapack, N.J.) in 50 mM sodium phosphate buffer, pH 7.0, and the flow through fraction collected. Thereafter, the serum proteins were eluted stepwise from the column using 50 mM sodium phosphate buffer, pH 7.0 containing increasing concentrations of sodium chloride. In this manner, 12 serum fractions were obtained, each containing a different amount of sodium chloride. The fractions included flow through, and elution buffers of 50 mM sodium phosphate buffer, pH 7.0 containing 25mM, 50 mM, 75mM, 100 mM, 125 mM, 150 mM, 200 mM, 250mM, 300 mM, 400 mM, and 2M sodium chloride.

The 50 mM sodium chloride fraction containing the protein of interest was subsequently buffer exchanged back into 50 mM sodium phosphate buffer, pH 7.0 and concentrated by means of a Centricon 10 (Millipore) in accordance with the manufacturer's instructions. The resulting sample then was fractionated by size exclusion chromatography on a Sephacryl S-200 column (Pharmacia) using an isocratic buffer containing 100 mM sodium phosphate, 150 mM NaCl, pH 7.4. Fractions that eluted from the column were evaluated for the presence of the 28.3 kD protein using the Ciphergen SELDI mass spectroscopy as described in Example 1. Fractions containing the 28.3 kD protein were pooled and applied to an IMAC column (Sigma) which had been pre-loaded with $Ni^{2+}$ by prior incubation with 50 mM $NiCl_2$. The IMAC column then was washed with 6 bed volumes of a solution containing 100 mM sodium phosphate, 150 mM NaCl, pH 7.4, and the bound protein fraction eluted with the same solution containing 100 mM imidazole. The eluted fraction then was concentrated by means of a Minicon 10 (Millipore) and then was fractionated by sodium dodecyl sulfate-polyacrylamide gel electrophoresis (SDS-PAGE) on a 12% Tris glycine SDS-PAGE gel. Samples of the protein fraction were applied to two separate lanes of the gel. After electrophoresis, the resulting gel then was stained with Coomassie Brilliant Blue dye and destained to reveal the presence of proteins. Three bands of about 28.3 kD (characterized as the heaviest molecular weight protein, the medium molecular weight protein, and the lightest molecular weight protein) were excised from one of the 2 lanes and were eluted from the acrylamide slices.

The proteins were eluted from the gel as follows. Briefly, the gel slices were washed five times with HPLC grade water with vigorous vortexing. The washed slices then were cut into small pieces in 120 µL of 100 mM sodium acetate pH 8.5, 0.1% SDS and incubated overnight at 37° C. The supernatant was decanted into a fresh tube and dried in a speedvac. The resulting pellet then was reconstituted in 37 µL HPLC grade water. Approximately 1480 µL of cold ethanol then was added and the resulting mixture incubated overnight at −20° C. The sample was centrifuged at 4° C. for 15 minutes at 11,000 rpm. The supernatant was removed and the resulting pellet reconstituted in 5 µL of water. The resulting protein solutions were run on the SELDI and the 28.3 kD protein was identified in one of the three preparations (see FIG. 1A which corresponds to the heaviest 28 kD protein). The corresponding band then was excised from the second of the 2 lanes on the gel. After proteolysis with trypsin, the tryptic fragments were eluted from the gel and submitted for microsequence analysis via mass spectrometry.

Four individual masses were detected by mass spectrometry. When the four masses were used to search the Swiss Protein Database, all four masses were found to match amino acid sequences present in the protein referred to in the art as U2 small nuclear ribonucleoprotein B" (U2 snRNP B") (Habets et al. (1987) supra, Swiss Protein Database Accession Number 4507123). The results are summarized in Table 2.

TABLE 2

| Peptide | Sequence | SEQ ID NO. | Protein |
|---|---|---|---|
| 1 | QLQGFPFYGKPMR | 1 | U2 snRNP B" |
| 2 | HDIAFVEFENDGQAGAAR | 2 | U2 snRNP B" |
| 3 | LVPGRHDIAFVEFENDGQAGAAR | 3 | U2 snRNP B" |
| 4 | TVEQTATTTNK | 4 | U2 snRNP B" |

The amino acid sequence, in an N- to C-terminal direction, of the U2 SnRNP B" protein in single amino acid code is:
MDIRPNHTIY INNMNDKIKK EELKRSLYAL FSQFGH-
  VVDI VALKTMKMRG QAFVIFKELG
SSTNALRQLQ GFPFYGKPMR IQYAKTDSDI ISKM-
  RGTFAD KEKKKEKKKA KTVEQTATTT
NKKPGQGTPN SANTQGNSTP NPQVPDYPPN YIL-
  FLNNLPE ETNEMMLSML FNQFPGFKEV
RLVPGRHDIA FVEFENDGQA GAARDALQGF KITP-
  SHAMKI TYAKK (SEQ ID NO: 5)

EXAMPLE 6

Purification and Characterization of 71 kD Breast Cancer Protein

The 71 kD breast cancer protein identified in Example 1 was isolated and further characterized as follows.

50 mL of serum from each of four individuals was pooled to give a single aliquot of 200 mL. This 200 mL aliquot was subdivided into six aliquots of 33 mL each. Each aliquot was treated with 19 mL of trifluorotrichloroethane as described in Example 1. Each aliquot was applied to Protein G and Cibacron Blue columns as described in Example 1. Fractions containing protein in the flowthrough (approximately 500 mL/aliquot) were pooled and concentrated to approximately 10 mL/aliquot (60 mL total) using Centricon concentrators.

3 mL aliquots were loaded onto 5 mL mono Q sepharose columns (60 mL/3 mL=20 aliquots). Fractionation was performed as described in Example 1, except that all volumes were multiplied by 5. The fractions eluted with 100 mM sodium chloride from each fractionation were pooled into a single 200 mL fraction and buffer exchanged into binding buffer as described in Example 1.

The 200 mL fraction was applied to a series of antibody columns to remove abundant proteins of 50–70 kD. Each of these proteins, alpha-1 anti-trypsin, ceruloplasmin, kallikrein, and GC-globulin, had been identified and sequenced during preliminary attempts to isolate the 71 kD protein. Commercial antibodies to each of the proteins were purchased and coupled to a solid support (agarose) using conventional NHS ester chemistry (Pierce Aminolink Plus kit—part number 44894). The 200 mL fraction was applied to each column in turn until the protein in question could no longer be seen in the flowthrough by Western blot analysis.

The flowthrough was subjected to size exclusion chromatography using an S200 column. Fractions containing the 71 kD peak were identified by SELDI as described in Example 1. Because these fractions also appeared to contain a fragment of human serum albumin (HSA) that would not bind to the Cibacron blue column, the fractions were applied to an HSA affinity column with two murine antibodies to HSA to depelete the remaining HSA from the sample. SDS-PAGE analysis of the sample revealed a single band in the 71 kD range by silver staining. The remaining sample was divided into two aliquots and run on two lanes of a 10% tris-glycine gel. The gel was stained with Coomassie Brilliant Blue dye. The 71 kD band from one of the two lanes was excised and eluted from the gel as described in Example 5. Its identity as the 70.972 kD marker protein was confirmed by SELDI. The 71 kD band from the other lane was excised and treated with trypsin. The resulting peptides were eluted from the gel and subjected to microsequence analysis by mass spectrometry. Sixteen of the predicted trypsin fragments of the 64-kD subunit of cleavage stimulation factor have masses corresponding to those identified in the mass spectrum of the 71 kD protein. The sixteen sequences are set forth in Table 3. Two reported sequences for cleavage stimulation factor are set forth in the Sequence Listing as SEQ ID NO:22 and SEQ ID NO:23.

TABLE 3

| Peptide | Sequence | SEQ ID NO. | Protein |
|---|---|---|---|
| 1 | GQVPMQDPR | 6 | Cleavage Stimulation Factor |
| 2 | GSLPANVPTPR | 7 | Cleavage Stimulation Factor |
| 3 | GLLGDAPNDPR | 8 | Cleavage Stimulation Factor |
| 4 | AGLTVRDPAVDR | 9 | Cleavage Stimulation Factor |
| 5 | ALRVDNAASEKNK | 10 | Cleavage Stimulation Factor |
| 6 | GGTLLSVTGEVEPR | 11 | Cleavage Stimulation Factor |
| 7 | DIFSEVGPVVSFR | 12 | Cleavage Stimulation Factor |
| 8 | GIDARGMEARAMEAR | 13 | Cleavage Stimulation Factor |
| 9 | GMEARAMEARGLDAR | 14 | Cleavage Stimulation Factor |
| 10 | AVASLPPEQMFELMK | 15 | Cleavage Stimulation Factor |
| 11 | AMEARAMEVRGMEAR | 16 | Cleavage Stimulation Factor |
| 12 | GYLGPPHQGPPMHHVPGHESR | 17 | Cleavage Stimulation Factor |
| 13 | GPIPSGMQGPSPINMGAVVPQGSR | 18 | Cleavage Stimulation Factor |
| 14 | NMLLQNPQLAYALLQAQVVMR | 19 | Cleavage Stimulation Factor |
| 15 | GGPLPEPRPLMAEPRGPMLDQR | 20 | Cleavage Stimulation Factor |
| 16 | SLGTGAPVIESPYGETISPEDAPESISK | 21 | Cleavage Stimulation Factor |

Equivalents

The invention may be embodied in other specific forms without departing from the spirit or essential characteristics thereof The foregoing embodiments are therefore to be considered in all respects illustrative rather than limiting on the invention described herein. Scope of the invention is thus indicated by the appended claims rather than by the foregoing description, and all changes that come within the meaning and range of equivalency of the claims are intended to be embraced by reference therein.

Incorporation By Reference

The entire disclosure of each of the aforementioned patent and scientific documents cited hereinabove is expressly incorporated by reference herein.

What is claimed is:

1. A method of diagnosing breast cancer in a mammal, the method comprising the steps of:
   (a) obtaining a sample isolated from the mammal; and
   (b) detecting in the sample the presence or absence of a protein characterized as comprising an amino acid sequence selected from the group consisting of SEQ ID NO: 1; SEQ ID NO: 2; SEQ ID NO: 3; SEQ ID NO: 4; and SEQ ID NO: 5, wherein the presence of the protein is indicative of the presence of breast cancer in the mammal, and wherein the absence of the protein is indicative of the absence of breast cancer in the mammal.

2. A method of diagnosing breast cancer in a mammal, the method comprising the step of:
   determining whether a protein comprising an amino acid sequence selected from the group consisting of SEQ ID NO:1, SEQ ID NO:2, SEQ ID NO:3, SEQ ID NO:4, and SEQ ID NO:5 is present in a sample derived from the mammal in an amount greater than or equal to a threshold value indicative of the presence of breast cancer in the mammal,
   wherein an amount of protein greater than or equal to the threshold value is indicative of the presence of breast cancer in the mammal and an amount of protein less than the threshold value is indicative of the absence of breast cancer in the mammal.

3. The method of claim 1 or 2, wherein the sample comprises breast tissue.

4. The method of claim 1 or 2, wherein the sample comprises a body fluid.

5. The method of claim 4, wherein the body fluid is selected from the group consisting of blood, serum, plasma, sweat, tears, urine, peritoneal fluid, lymph, vaginal secretions, semen, spinal fluid, ascitic fluid, saliva, sputum, and breast exudate.

6. A method of diagnosing breast cancer in a mammal, the method comprising the steps of:
   (a) contacting a sample derived from the mammal with a binding moiety that binds specifically to a protein comprising an amino acid sequence of SEQ ID NO: 5, thereby to produce a complex; and
   (b) detecting the presence or absence of a complex, wherein the presence of the complex is indicative of the presence of breast cancer in the mammal, and wherein the absence of the complex is indicative of the absence of breast cancer in the mammal.

7. A method of diagnosing breast cancer in a mammal, the method comprising the steps of:
   (a) contacting a sample from the mammal derived from the mammal with a binding moiety that binds specifically to a protein comprising an amino acid sequence of SEQ ID NO:5, thereby to produce a complex; and
   (b) determining whether the complex is present in an amount greater than or equal to a threshold value indicative of the presence of breast cancer in the mammal,
   wherein an amount greater than or equal to the threshold value is indicative of the presence of breast cancer in the mammal and an amount less than the threshold value is indicative of the absence of breast cancer in the mammal.

8. The method of claim 6 or 7, wherein the binding moiety is selected from the group consisting of an antibody, an antibody fragment and a biosynthetic antibody binding site.

9. The method of claim 6 or 7, wherein the binding moiety is an antibody.

10. The method of claim 9, wherein, the antibody is a monoclonal antibody.

11. The method of claim 8, wherein the binding moiety is labeled with a detectable moiety.

12. The method of claim 6, wherein the absence of a detectable amount of the complex is indicative of the absence of breast cancer.

13. The method of claim 4, wherein the body fluid is serum.

14. The method of claim 6 or 7, wherein the sample comprises breast tissue.

15. The method of claim 6 or 7, wherein the sample comprises a body fluid.

16. The method of claim 15, wherein the body fluid is selected from the group consisting of blood, serum, plasma, sweat, tears, urine, peritoneal fluid, lymph, vaginal secretions, semen, spinal fluid, ascitic fluid, saliva, sputum, and breast exudate.

17. The method of claim 15, wherein the body fluid is serum.

18. The method of claim 1, wherein the presence of a detectable amount of the protein is indicative of the presence of breast cancer in the mammal.

19. The method of claim 1, wherein the absence of a detectable amount of the protein is indicative of the absence of breast cancer in the mammal.

* * * * *

UNITED STATES PATENT AND TRADEMARK OFFICE
CERTIFICATE OF CORRECTION

PATENT NO. : 6,936,424 B1
DATED : August 30, 2005
INVENTOR(S) : Watkins et al.

It is certified that error appears in the above-identified patent and that said Letters Patent is hereby corrected as shown below:

Title page,
Item [60], Related U.S. Application Data, delete "60/165,173, filed on Nov. 12, 1999" and insert -- 60/165,673, filed on Nov. 16, 1999 --.

Column 46,
Line 50, delete "wherein,the" and insert -- wherein the --.

Signed and Sealed this

Fourteenth Day of March, 2006

JON W. DUDAS
*Director of the United States Patent and Trademark Office*